United States Patent
Ganapathy-Kanniappan

(10) Patent No.: US 11,191,816 B2
(45) Date of Patent: Dec. 7, 2021

(54) MUTANT GLYCERALDEHYDE-3-PHOSPHATE DEHYDROGENASE (GAPDH) COMPOSITIONS AND METHODS OF TREATING CANCER

(71) Applicant: THE JOHNS HOPKINS UNIVERSITY, Baltimore, MD (US)

(72) Inventor: Shanmugasundaram Ganapathy-Kanniappan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 36 days.

(21) Appl. No.: 16/071,527

(22) PCT Filed: Jan. 19, 2017

(86) PCT No.: PCT/US2017/014055
§ 371 (c)(1),
(2) Date: Jul. 20, 2018

(87) PCT Pub. No.: WO2017/127498
PCT Pub. Date: Jul. 27, 2017

(65) Prior Publication Data
US 2019/0022191 A1 Jan. 24, 2019

Related U.S. Application Data

(60) Provisional application No. 62/280,987, filed on Jan. 20, 2016.

(51) Int. Cl.
*A61K 38/44* (2006.01)
*C12N 9/00* (2006.01)
*A61P 35/00* (2006.01)
*A61K 38/00* (2006.01)
*A61K 31/282* (2006.01)
*A61K 31/395* (2006.01)
*A61K 45/06* (2006.01)
*C12N 9/02* (2006.01)

(52) U.S. Cl.
CPC .............. *A61K 38/44* (2013.01); *A61P 35/00* (2018.01); *C12N 9/0008* (2013.01); *C12Y 102/01012* (2013.01); *A61K 31/282* (2013.01); *A61K 31/395* (2013.01); *A61K 38/00* (2013.01); *A61K 45/06* (2013.01); *A61K 2300/00* (2013.01)

(58) Field of Classification Search
None
See application file for complete search history.

(56) References Cited

U.S. PATENT DOCUMENTS 5,290,690 A * 3/1994 Mrabet ................ C12N 9/0008
435/189

FOREIGN PATENT DOCUMENTS

| CA | 2244323 A1 | 9/1998 |
| EP | 2559758 A1 | 2/2013 |
| JP | 2014035186 A * | 2/2014 |
| WO | 01/94591 A1 | 12/2001 |
| WO | 2005049793 A2 | 2/2005 |

OTHER PUBLICATIONS

Jenkins et al., "High-resolution structure of human D-glyceraldehyde-3-phosphate dehydrogenase", Acta Cryst.D, 2006, D62, pp. 290-301.*
Berge et al., (1977) "Pharmaceutical Salts", J. Pharm. Sci. 66:1-19.
Hanahan et al., Hallmarks of cancer: The next generation. Cell. 2011; 144: 646-74.
Warburg., On the origin of cancer cells.—Science.Feb. 24, 1956;123(3191):309-14.
Huge-Wissemann et al., Differences in glycolytic capacity and hypoxia tolerance between hepatoma cells and hepatocytes. Hepatology. 1991; 13: 297-303.
Ganapathy-Kanniappan et al., Human hepatocellular carcinoma in a mousemodel: Assessment of tumor response to percutaneous ablation by using glyceraldehyde-3-phosphate dehydrogenase antagonists. Radiology. 2012; 262: 834-45.
Kim et al., Antisense oligodeoxynucleotide of glyceraldehyde-3-phosphate dehydrogenase gene inhibits cell proliferation and induces apoptosis in human cervical carcinoma cell lines. Antisense Nucleic Acid Drug Dev. 1999; 9: 507-13.
Phadke et al., Glyceraldehyde 3-phosphate dehydrogenase depletion induces cell cycle arrest and resistance to antimetabolites in human carcinoma cell lines. J Pharmacol Exp Ther. 2009; 331: 77-86.
Tyson et al., Level of alpha-fetoprotein predicts mortality among patients with hepatitis C-related hepatocellular carcinoma. Clin Gastroenterol Hepatol. 2011, 9:989-994.
Ganapathy-Kanniappan et al., Glyceraldehyde-3-phosphate dehydrogenase (GAPDH) is pyruvylated during 3-bromopyruvate mediated cancer cell death. Anticancer Res. 2009; 29:4909-18.
Franken et al., Clonogenic assay of cells in vitro. Nat Protoc. 2006; 1: 2315-9.
Jang et al., Cancer cell metabolism: Implications for therapeutic targets. Exp Mol Med. 2013; 45: e45.
Zhao et al., Targeting cellular metabolism to improve cancer therapeutics. Cell Death Dis. 2013; 4: e532.
Dang., Links between metabolism and cancer. Genes Dev. 2012; 26: 877-90.

(Continued)

*Primary Examiner* — Suzanne M Noakes
(74) *Attorney, Agent, or Firm* — Johns Hopkins Technology Ventures

(57) ABSTRACT

Provided herein are compositions comprising mutant GADPH. Methods for treating or preventing cancer in a subject by administering to the subject a therapeutically effective amount of mutant GAPDH compositions are provided.

4 Claims, 28 Drawing Sheets
Specification includes a Sequence Listing.

(56) References Cited

OTHER PUBLICATIONS

Ganapathy-Kanniappan et al., Tumor glycolysis as a target for cancer therapy: Progress and prospects. Mol Cancer. 2013; 12: 152,4598-12-152.

Ganapathy-Kanniappan et al., Glyceraldehyde-3-phosphate dehydrogenase: A promising target for molecular therapy in hepatocellular carcinoma. Oncotarget. 2012; 3: 940-53.

El-Serag., Hepatocellular carcinoma. N Engl J Med. 2011; 365: 1118-27.

Kitamura et al., Proliferative activity in hepatocellular carcinoma is closely correlated with glucose metabolism but not angiogenesis. J Hepatol. 2011; 55: 846-57.

Fritz et al., Metabolism and proliferation share common regulatory pathways in cancer cells. Oncogene. 2010; 29: 4369-77.

Gong et al., Comparison of glyceraldehyde-3-phosphate dehydrogenase and 28s-ribosomal RNA gene expression in human hepatocellular carcinoma. Hepatology. 1996; 23: 734-7.

Lau et al., Differential gene expression of hepatocellular carcinoma using cDNA microarray analysis. Oncol Res. 2000; 12: 59-69.

Sirover., On the functional diversity of glyceraldehyde-3-phosphate dehydrogenase: Biochemical mechanisms and regulatory control. Biochim Biophys Acta. 2011; 1810: 741-51.

Tristan et al.. The diverse functions of GAPDH: Views from different subcellular compartments. Cell Signal. 2011; 23: 317-23.

Gharwan et al.. Kinase inhibitors and monoclonal antibodies in oncology: clinical implications., Nat. Rev. Clin. Oneal. (2015), 13:209.

Rothenberg et al., Improving the evaluation of new cancer treatments: challenges and opportunities., Nat. Rev. Cancer. 3, 303-309 (2003).

Trouneau et al.. Current challenges for the early clinical development of anticancer drugs in the era of molecularly targeted agents., Targeted Oncology 5, 65-72 (2010).

Pecot et al., RNA interference in the clinic: challenges and future directions., Nat. Rev. Cancer. 11, 59-67 (2011).

Rayburn et al., Antisense, RNAi, and gene silencing strategies for therapy: Mission possible or impossible?., Drug Discov. Today 13, 513-521 (2008).

Gambhir., (2002) Molecular imaging of cancer with positron emission tomography. Nat Rev Cancer 2: 683-693.

Fan et al., (2010) Akt inhibitors reduce glucose uptake independently of their effects on Akt. Biochem J 432: 191-197.

Kunjithapatham et al., (2015) Occurrence of a Multimeric High-Molecular-Weight Glyceraldehyde-3-phosphate Dehydrogenase in Human Serum J Proteome Res 14: 1645-1656.

Maher et al., (2007) Hypoxia-inducible factor-I confers resistance to the glycolytic inhibitor 2-deoxy-Dglucose. Mol Cancer Ther 6: 732-741.

Mikhaylova et al., (2008) Hypoxia increases breast cancer cell-induced lymphatic endothelial cell migration. Neoplasia 10: 380-389.

\* cited by examiner

Figure 17
(a) GAPDH (wild type) enzymatic action during glycolysis
(b) Competitive inhibition by ectopically expressed mutant GAPDH
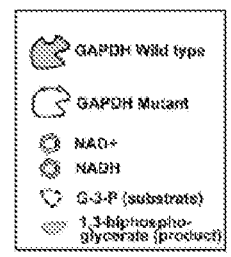

Figure 18
(a)
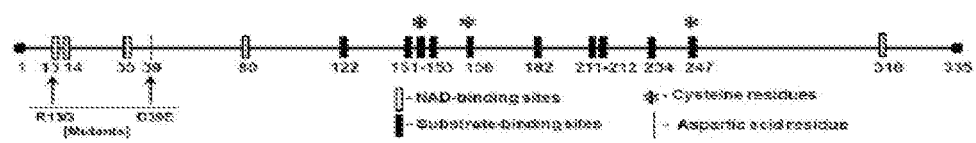
(b)
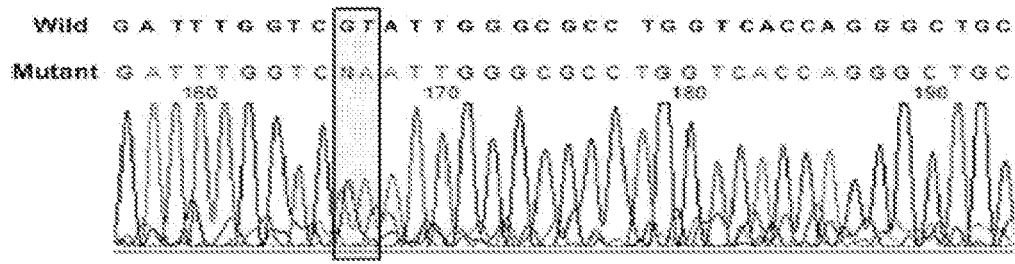
(c)
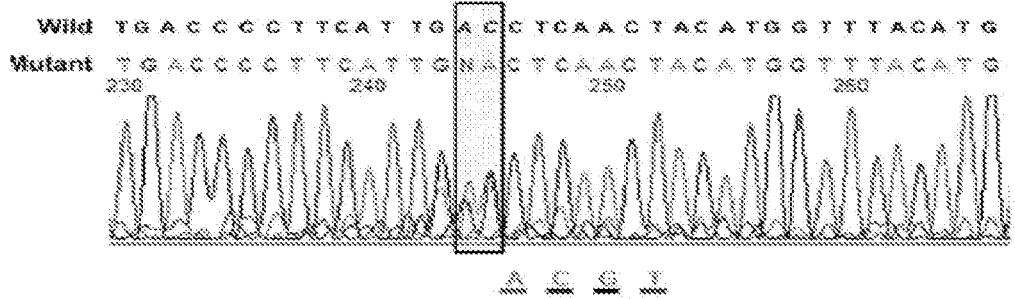
Figure 18 (b) Wild:     SEQ ID NO: 21
Figure 18 (b) Mutant: SEQ ID NO: 22
Figure 18 (c) Wild:     SEQ ID NO: 23
Figure 18 (c) Mutant  SEQ ID NO: 24

Figure 20

Primer design for site-directed mutagenesis

Amino acid position:    1   2   3   4   5   6   7   8   9   10   11   12   13   14   15

Wild type:          atg ggg aag gtg aag gtc gga gtc aac gga ttt ggt cgt att ggg
                    (SEQ ID NO: 11)

M   G   K   V   K   V   G   V   N   G   F   G   R   I   G
                    (SEQ ID NO:12)

Mutant R13Q:    atg ggg aag gtg aag gtc gga gtc aac gga ttt ggt *caa* att ggg
                    (SEQ ID NO:13)

M   G   K   V   K   V   G   V   N   G   F   G   *Q*   I   G
                    (SEQ ID NO: 14)

Amino acid position:    31  32  33  34  35  36  37  38  39  40  41  42  43  44  45

Wild type:          gtt gcc atc aat gac ccc ttc att gac ctc aac tac atg gtt tac
                    (SEQ ID NO:15)

V   A   I   N   D   P   F   I   D   L   N   Y   M   V   Y
                    (SEQ ID NO:16)

Mutant D39E:    gtt gcc atc aat gac ccc ttc att *gaa* ctc aac tac atg gtt tac
                    (SEQ ID NO:17)

V   A   I   N   D   P   F   I   *E*   L   N   Y   M   V   Y
                    (SEQ ID NO:18)

SEQ ID NO: 19

SEQ ID NO: 20

SEQUENCE LISTING

<160> NUMBER OF SEQ ID NOS: 28

<210> SEQ ID NO 1
<211> LENGTH: 1008
<212> TYPE: DNA
<213> ORGANISM: Homo sapiens

<400> SEQUENCE: 1

```
atggggaagg tgaaggtcgg agtcaacgga tttggtcgtt ttgggcgcct ggtcaccagg    60
gctgctttta actctggtaa agtggatatt gttgccatca atgacccctt cattgacctc   120
aactacatgg tttacatgtt ccaatatgat tccacccatg gcaaattcca tggcaccgtc   180
```

-continued

```
aaggctgaga acgggaagct tgtcatcaat ggaaatccca tcaccatctt ccaggagcga   240
gatccctcca aaatcaagtg ggcgatgctg gcgctgagt acgtcgtgga gtccactggc   300
gtcttcacca ccatggagaa ggctggggct catttgcagg ggggagccaa aagggtcatc   360
atctctgccc cctctgctga tgcccccatg ttcgtcatgg gtgtgaacca tgagaagtat   420
gacaacagcc tcaagatcat cagcaatgcc tcctggacca ccaactggtt agcacccctg   480
gccaaggtca tccatgacaa ctttggtatc gtggaaggac tcatgaccac agtccttgcc   540
atcactgcca cccagaagac tgtggatggc ccctccggga actgtggcg tgatggccgc   600 ggggctctcc agaacatcat ccctgcctct actggcgctg ccaaggctgt gggcaaggtc   660
atccctgagc tgaacgggaa gctcactggc atggccttcc gtgtcccac tgccaacgtg   720 tcagtggtgg acctgacctg ccgtctagaa aaacctgcca atatgatga catcaagaag   780 gtggtgaagc aggcgtcgga gggccccctc aagggcatcc tgggctacac tgagcaccag   840
gtggtctcct ctgacttcaa cagcgacacc cactcctcca cctttgacgc tggggctggc   900
attgccctca cgaccacttt tgtcaagctc atttcctggt atgacaagga atttggctac   960
agcaacaggg tggtggacct catggcccac atggcctcca aggagtaa              1008
```

<210> SEQ ID NO 2
<211> LENGTH: 335
<212> TYPE: PRT
<213> ORGANISM: Homo sapiens

<400> SEQUENCE: 2

```
Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val
```

```
                225                 230                 235                 240
Ser Val Val Asp Leu Thr Cys Arg Leu Glu Lys Pro Ala Lys Tyr Asp
                    245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu
                325                 330                 335

<210> SEQ ID NO 3
<211> LENGTH: 1008
<212> TYPE: DNA
<213> ORGANISM: Homo sapiens

<400> SEQUENCE: 3
atggggaagg tgaaggtcgg agtcaacgga tttggtcaaa ttgggcgcct ggtcaccagg      60
gctgctttta actctggtaa agtggatatt gttgccatca atgacccctt cattgacctc     120
aactacatgg tttacatgtt ccaatatgat tccacccatg gcaaattcca tggcaccgtc     180
aaggctgaga cgggaagct tgtcatcaat ggaaatccca tcaccatctt ccaggagcga     240
gatccctcca aaatcaagtg gggcgatgct ggcgctgagt acgtcgtgga gtccactggc     300
gtcttcacca ccatggagaa ggctggggct catttgcagg ggggagccaa agggtcatc     360 atctctgccc cctctgctga tgcccccatg ttcgtcatgg gtgtgaacca tgagaagtat     420
gacaacagcc tcaagatcat cagcaatgcc tcctggacca ccaactggtt agcacccctg     480
gccaaggtca tccatgacaa ctttggtatc gtggaaggac tcatgaccac agtccttgcc     540
atcactgcca cccagaagac tgtggatggc ccctccggga aactgtggcg tgatggccgc     600
ggggctctcc agaacatcat ccctgcctct actggcgctg ccaaggctgt gggcaaggtc     660
atccctgagc tgaacgggaa gctcactggc atggccttcc gtgtccccac tgccaacgtg     720
tcagtggtgg acctgacctg ccgtctagaa aaacctgcca aatatgatga catcaagaag     780
gtggtgaagc aggcgtcgga gggcccctc aagggcatcc tgggctacac tgagcaccag     840
gtggtctcct ctgacttcaa cagcgacacc cactcctcca cctttgacgc tggggctggc     900
attgccctca cgaccacttt gtcaagctc atttcctggt atgacaagga atttggctac     960
agcaacaggg tggtggacct catggcccac atggcctcca aggagtaa                1008

<210> SEQ ID NO 4
<211> LENGTH: 335
<212> TYPE: PRT
<213> ORGANISM: Homo sapiens

<400> SEQUENCE: 4

Met Gly Lys Val Lys Val Gly Val Asn Gly Phe Gly Gln Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45
```

```
Tyr Asp Ser Thr His Gly Lys Phe His Gly Thr Val Lys Ala Glu Asn
    50                  55                  60
Gly Lys Leu Val Ile Asn Gly Asn Pro Ile Thr Ile Phe Gln Glu Arg
 65                  70                  75                  80
Asp Pro Ser Lys Ile Lys Trp Gly Asp Ala Gly Ala Glu Tyr Val Val
                 85                  90                  95
Glu Ser Thr Gly Val Phe Thr Thr Met Glu Lys Ala Gly Ala His Leu
            100                 105                 110
Gln Gly Gly Ala Lys Arg Val Ile Ile Ser Ala Pro Ser Ala Asp Ala
        115                 120                 125
Pro Met Phe Val Met Gly Val Asn His Glu Lys Tyr Asp Asn Ser Leu
130                 135                 140
Lys Ile Ile Ser Asn Ala Ser Cys Thr Thr Asn Cys Leu Ala Pro Leu
145                 150                 155                 160
Ala Lys Val Ile His Asp Asn Phe Gly Ile Val Glu Gly Leu Met Thr
                165                 170                 175
Thr Val His Ala Ile Thr Ala Thr Gln Lys Thr Val Asp Gly Pro Ser
            180                 185                 190
Gly Lys Leu Trp Arg Asp Gly Arg Gly Ala Leu Gln Asn Ile Ile Pro
        195                 200                 205
Ala Ser Thr Gly Ala Ala Lys Ala Val Gly Lys Val Ile Pro Glu Leu
210                 215                 220
Asn Gly Lys Leu Thr Gly Met Ala Phe Arg Val Pro Thr Ala Asn Val
225                 230                 235                 240
Ser Val Val Asp Leu Thr Cys Arg Leu Glu Lys Pro Ala Lys Tyr Asp
                245                 250                 255
Asp Ile Lys Lys Val Val Lys Gln Ala Ser Glu Gly Pro Leu Lys Gly
            260                 265                 270
Ile Leu Gly Tyr Thr Glu His Gln Val Val Ser Ser Asp Phe Asn Ser
        275                 280                 285
Asp Thr His Ser Ser Thr Phe Asp Ala Gly Ala Gly Ile Ala Leu Asn
290                 295                 300
Asp His Phe Val Lys Leu Ile Ser Trp Tyr Asp Asn Glu Phe Gly Tyr
305                 310                 315                 320
Ser Asn Arg Val Val Asp Leu Met Ala His Met Ala Ser Lys Glu
                325                 330                 335

<210> SEQ ID NO 5
<211> LENGTH: 1008
<212> TYPE: DNA
<213> ORGANISM: Homo sapiens

<400> SEQUENCE: 5
atggggaagg tgaaggtcgg agtcaacgga tttggtcaaa ttgggcgcct ggtcaccagg      60
gctgctttta actctggtaa agtggatatt gttgccatca atgacccctt cattgaactc     120
aactacatgg tttacatgtt ccaatatgat tccacccatg gcaaattcca tggcaccgtc     180
aaggctgaga cgggaagct tgtcatcaat ggaaatccca tcaccatctt ccaggagcga     240
gatccctcca aaatcaagtg gggcgatgct ggcgctgagt acgtcgtgga gtccactggc     300
gtcttcacca ccatggagaa ggctgggct catttgcagg ggggagccaa aagggtcatc     360
atctctgccc cctctgctga tgcccccatg ttcgtcatgg gtgtgaacca tgagaagtat     420
gacaacagcc tcaagatcat cagcaatgcc tcctggacca ccaactggtt agcacccctg     480
gccaaggtca tccatgacaa ctttggtatc gtggaaggac tcatgaccac agtccttgcc     540
```

```
atcactgcca cccagaagac tgtggatggc ccctccggga aactgtggcg tgatggccgc     600
ggggctctcc agaacatcat ccctgcctct actggcgctg ccaaggctgt gggcaaggtc     660
atccctgagc tgaacgggaa gctcactggc atggccttcc gtgtcccac tgccaacgtg      720 tcagtggtgg acctgaccctg ccgtctagaa aaacctgcca aatatgatga catcaagaag    780
gtggtgaagc aggcgtcgga gggccccctc aagggcatcc tgggctacac tgagcaccag     840
gtggtctcct ctgacttcaa cagcgacacc cactcctcca cctttgacgc tggggctggc     900
attgccctca acgaccactt tgtcaagctc atttcctggt atgacaagga atttggctac    960
agcaacaggg tggtggacct catggcccac atggcctcca aggagtaa                1008
```

<210> SEQ ID NO 6
<211> LENGTH: 335
<212> TYPE: PRT
<213> ORGANISM: Homo sapiens

<400> SEQUENCE: 6

```
Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Glu Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285
```

```
Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu
                325                 330                 335

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcaacggatt tggtcaattt gggcgcctgg tca                                33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgaccaggcg cccaaattga ccaaatccgt tga                                33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aatgacccct tcattagact caactacatg gtt                                33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaccatgtag ttgagtctaa tgaaggggtc att                                33

<210> SEQ ID NO 11
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 11 atg ggg aag gtg aag gtc gga gtc aac gga ttt ggt cgt att ggg        45
Met Gly Lys Val Lys Val Gly Val Asn Gly Phe Gly Arg Ile Gly
1               5                   10                  15

<210> SEQ ID NO 12
<211> LENGTH: 15
```

```
<212> TYPE: PRT
<213> ORGANISM: Homo sapiens

<400> SEQUENCE: 12

Met Gly Lys Val Lys Val Gly Val Asn Gly Phe Gly Arg Ile Gly
1               5                   10                  15

<210> SEQ ID NO 13
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 13 atg ggg aag gtg aag gtc gga gtc aac gga ttt ggt caa att ggg       45
Met Gly Lys Val Lys Val Gly Val Asn Gly Phe Gly Gln Ile Gly
1               5                   10                  15

<210> SEQ ID NO 14
<211> LENGTH: 15
<212> TYPE: PRT
<213> ORGANISM: Homo sapiens

<400> SEQUENCE: 14

Met Gly Lys Val Lys Val Gly Val Asn Gly Phe Gly Gln Ile Gly
1               5                   10                  15

<210> SEQ ID NO 15
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 15 gtt gcc atc aat gac ccc ttc att gac ctc aac tac atg gtt tac       45
Val Ala Ile Asn Asp Pro Phe Ile Asp Leu Asn Tyr Met Val Tyr
1               5                   10                  15

<210> SEQ ID NO 16
<211> LENGTH: 15
<212> TYPE: PRT
<213> ORGANISM: Homo sapiens

<400> SEQUENCE: 16

Val Ala Ile Asn Asp Pro Phe Ile Asp Leu Asn Tyr Met Val Tyr
1               5                   10                  15

<210> SEQ ID NO 17
<211> LENGTH: 45
<212> TYPE: DNA
<213> ORGANISM: Homo sapiens
<220> FEATURE:
<221> NAME/KEY: CDS
<222> LOCATION: (1)..(45)

<400> SEQUENCE: 17 gtt gcc atc aat gac ccc ttc att gaa ctc aac tac atg gtt tac       45
Val Ala Ile Asn Asp Pro Phe Ile Glu Leu Asn Tyr Met Val Tyr
1               5                   10                  15

<210> SEQ ID NO 18
<211> LENGTH: 15
<212> TYPE: PRT
```

<213> ORGANISM: Homo sapiens

<400> SEQUENCE: 18

Val Ala Ile Asn Asp Pro Phe Ile Glu Leu Asn Tyr Met Val Tyr
1               5                   10                  15

<210> SEQ ID NO 19
<211> LENGTH: 221
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
atgctcaaga tcatcagcaa tgcctcctgc accaccaact gcttagcacc cctggccaag     60
gtcatccatg acaactttgg tatcgtggaa ggactcatga ccacagtcca tgccatcact    120
gcacccagaa gactgtggat ggcccctccg ggaaactgtg gcgtgatggc cgcggggctc    180
tccagaacat catccctgcc tctactggcg ctgccaagta a                        221
```

<210> SEQ ID NO 20
<211> LENGTH: 316
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgctcaaga tcatcagcaa tgcctcctgc accaccaact gcttagcacc cctggccaag     60
gtcatccatg acaactttgg tatcgtggaa ggactcatga ccacagtcca tgccatcact    120
gcacccagaa gactgtggat ggcccctccg ggaaactgtg gcgtgatggc cgcggggctc    180
tccagaacat catccctgcc tctactggcg ctgccaaggc tgtgggcaag gtcatccctg    240
agctgaacgg aagctcactg gcatggcctt ccgtgtcccc actgccaacg tgtcagtggt    300
ggacctgacc tgctaa                                                    316
```

<210> SEQ ID NO 21
<211> LENGTH: 37
<212> TYPE: DNA
<213> ORGANISM: Homo sapiens

<400> SEQUENCE: 21

```
gatttggtcg tattgggcgc ctggtcacca gggctgc                              37
```

<210> SEQ ID NO 22
<211> LENGTH: 37
<212> TYPE: DNA
<213> ORGANISM: Homo sapiens
<220> FEATURE:
<221> NAME/KEY: modified_base
<222> LOCATION: (10)..(10)
<223> OTHER INFORMATION: a, c, t, g, unknown or other

<400> SEQUENCE: 22

```
gatttggtcn aattgggcgc ctggtcacca gggctgc                              37
```

<210> SEQ ID NO 23
<211> LENGTH: 37
<212> TYPE: DNA
<213> ORGANISM: Homo sapiens

<400> SEQUENCE: 23 tgacccttc attgacctca actacatggt ttacatg     37

<210> SEQ ID NO 24
<211> LENGTH: 37
<212> TYPE: DNA
<213> ORGANISM: Homo sapiens
<220> FEATURE:
<221> NAME/KEY: modified_base
<222> LOCATION: (15)..(15)
<223> OTHER INFORMATION: a, c, t, g, unknown or other

<400> SEQUENCE: 24 tgacccttc attgnactca actacatggt ttacatg     37

<210> SEQ ID NO 25
<211> LENGTH: 216
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25
ctcaagatca tcagcaatgc ctcctgcacc accaactgct tagcacccct ggccaaggtc     60
atccatgaca actttggtat cgtggaagga ctcatgacca cagtccatgc catcactgcc    120
acccagaaga ctgtggatgg ccccctccggg aaactgtggc gtgatggccg cggggctctc    180
cagaacatca tccctgcctc tactggcgct gccaag                               216

<210> SEQ ID NO 26
<211> LENGTH: 72
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Leu Lys Ile Ile Ser Asn Ala Ser Cys Thr Thr Asn Cys Leu Ala Pro
1               5                   10                  15

Leu Ala Lys Val Ile His Asp Asn Phe Gly Ile Val Glu Gly Leu Met
            20                  25                  30

Thr Thr Val His Ala Ile Thr Ala Thr Gln Lys Thr Val Asp Gly Pro
        35                  40                  45

Ser Gly Lys Leu Trp Arg Asp Gly Arg Gly Ala Leu Gln Asn Ile Ile
    50                  55                  60

Pro Ala Ser Thr Gly Ala Ala Lys
65                  70

<210> SEQ ID NO 27
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27
ctcaagatca tcagcaatgc ctcctgcacc accaactgct tagcacccct ggccaaggtc     60
atccatgaca actttggtat cgtggaagga ctcatgacca cagtccatgc catcactgcc    120
acccagaaga ctgtggatgg ccccctccggg aaactgtggc gtgatggccg cggggctctc    180

```
cagaacatca tccctgcctc tactggcgct gccaaggctg tgggcaaggt catccctgag    240
ctgaacggga agctcactgg catggccttc cgtgtcccca ctgccaacgt gtcagtggtg    300
gacctgacct gc                                                        312
```

```
<210> SEQ ID NO 28
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Leu Lys Ile Ile Ser Asn Ala Ser Cys Thr Thr Asn Cys Leu Ala Pro
1               5                   10                  15

Leu Ala Lys Val Ile His Asp Asn Phe Gly Ile Val Glu Gly Leu Met
            20                  25                  30

Thr Thr Val His Ala Ile Thr Ala Thr Gln Lys Thr Val Asp Gly Pro
        35                  40                  45

Ser Gly Lys Leu Trp Arg Asp Gly Arg Gly Ala Leu Gln Asn Ile Ile
    50                  55                  60

Pro Ala Ser Thr Gly Ala Ala Lys Ala Val Gly Lys Val Ile Pro Glu
65                  70                  75                  80

Leu Asp Gly Lys Leu Thr Gly Met Ala Phe Arg Val Pro Thr Ala Asn
                85                  90                  95

Val Ser Val Val Asp Leu Thr Cys
            100
```

MUTANT GLYCERALDEHYDE-3-PHOSPHATE DEHYDROGENASE (GAPDH) COMPOSITIONS AND METHODS OF TREATING CANCER

CROSS-REFERENCE TO RELATED APPLICATIONS

This application is a 35 U.S.C. § 371 U.S. national entry of International Application PCT/US2017/014055 having an international filing date of 19 Jan. 2017, which claims the benefit of U.S. Provisional Application No. 62/280,987, filed 20 Jan. 2016, the content of each of the aforementioned applications is herein incorporated by reference in their entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jan. 18, 2017, is named P13350-02_ST25.txt and is 20,966 bytes in size.

BACKGROUND OF THE INVENTION

One of the hallmarks of cancer is that cancer cells exhibit a metabolic reprogramming (1). Among various metabolic alterations, glycolysis [i.e. the process of conversion of glucose into pyruvate followed by lactate] has long been known to be part of cancer cells' biochemical adaptation. In normal cell metabolism, the process of glycolysis occurs as a compensatory mechanism during diminished oxygen supply, hence referred as "anaerobic glycolysis". However, in cancer cells glycolysis has been witnessed even in the presence of oxygen hence known as "aerobic glycolysis". This metabolic phenotype of aerobic glycolysis has been reported almost 90 years ago by the German scientist Otto Warburg (2). One of the key enzymes of glycolysis is GAPDH (abbreviated for glyceraldehyde-3-phosphate dehydrogenase), that catalyzes the first step of energy rich/redox molecule (NADH) producing reaction. Further, GAPDH also acts as a redox modifier due to its role in the regulation of NAD/NADH and NADP/NADPH ratio. Besides, emerging data also indicate that GAPDH is involved in several non-glycolytic processes underscoring its pivotal role in cell survival. HCC has been known to express elevated levels of GAPDH and this up regulation has been linked to glycolytic capacity of cancer cells (3).

One of the major challenges of successful and effective targeting of a cancer-related or cancer-specific molecule (e.g. gene, protein, and enzyme) is the lack of specificity. Current chemotherapeutics and agents under preclinical validation are effective in the inhibition of a chosen molecule but are not specific to the target. This, in fact, is the principal causal factor for the unwanted and undesirable toxicities experienced with chemotherapeutics in general. While the gene therapeutic strategies such as shRNA or siRNA are very specific to the molecular target but their selective delivery to the tumor is a major challenge. Furthermore, the siRNA has the limitation of inactivating or neutralizing the target at 1:1 ratio which would necessitate a constant and high levels of delivery of specific RNA to the tumor. The shRNA on the other hand, once introduced into the tumor, could integrate into host genome and produce a continuous antisense oligos that can interfere with specific target. However, the robust expression of shRNA in general requires pol (polymerase) III promoters such as H1 and/or U6 promoters. Unfortunately, these promoters are not tumor specific and are limited in their application via systemic therapy.

Preclinical reports indicate that molecular targeting of cancer significantly improves therapeutic efficacy (22). Yet, successful clinical translation of majority of anticancer agents remains a challenge (23, 24). Although nucleic acid-based, antisense therapeutic approaches (e.g. siRNA, shRNA) enjoy superiority in molecular specificity and effective inhibition certain inherent limitations hamper their success towards clinical application (13, 25).

Accordingly, there is a great need in the art to identify potential therapeutic strategies and compositions that target energy metabolism in the treatment of cancer.

SUMMARY OF THE INVENTION

The present invention provides at least in part a method for preventing, inhibiting, or treating cancer in a subject in need of treatment thereof, the method comprising administering to the subject a therapeutically effective amount of one or more mutant GAPDH.

One aspect of the invention relates to an isolated nucleic acid molecule which encodes a glyceraldehyde-3-phosphate dehydrogenase (GAPDH), said GAPDH comprises at least one mutation. In certain embodiments, the GAPDH has at least two, three, four, five, or six mutations. In certain embodiments, the GAPDH has at least one mutation, said mutation is an Arginine to Glutamine at position 13 (R13Q). In certain embodiments, the GAPDH has at least one mutation, said mutation is an Aspartic Acid to Glutamic Acid at position 39 (D39E). In certain embodiments, the GAPDH comprises a nucleotide sequence having at least 80% identity to the nucleotide sequence set forth in SEQ ID NO: 3 or 5. Another aspect of the invention relates to a pharmaceutical composition comprising the isolated nucleic acid molecule as described herein, in combination with a pharmaceutically acceptable carrier or adjuvant.

One aspect of the invention relates to an isolated polypeptide molecule comprising a mutant GAPDH, said GAPDH comprises at least one mutation. In certain embodiments, the GAPDH has at least two, three, four, five, or six mutations. In certain embodiments, the GAPDH has at least one mutation, said mutation is an Arginine to Glutamine at position 13 (R13Q). In certain embodiments, the GAPDH has at least one mutation, said mutation is an Aspartic Acid to Glutamic Acid at position 39 (D39E). In certain embodiments, the GAPDH comprises amino sequence having at least 80% identity to the amino acid sequence set forth in SEQ ID NO: 4 or 6. Another aspect of the invention relates to a pharmaceutical composition comprising the isolated polypeptide molecule as described herein, in combination with a pharmaceutically acceptable carrier or adjuvant.

Another aspect of the invention relates to an expression vector comprising an isolated nucleic acid molecule as described herein operably linked to a tumor-specific promoter. In certain embodiments, the tumor-specific promoter is selected from the group consisting of hTERT, Cholecystokinin A Receptor (CCKAR), and Alpha feto protein (AFP). Another aspect of the invention relates to a pharmaceutical composition comprising expression vector as described herein in combination with a pharmaceutically acceptable carrier or adjuvant.

One aspect of the invention relates to a method for preventing or treating cancer in a subject, the method comprising administering to the subject a therapeutically effective amount of any of the pharmaceutical composition of the mutant (mt)-GAPDH as described herein. In certain embodiments, the composition is administered systematically. In certain embodiments, the systematic administration is selected from the group consisting of oral, intravenous, intraperitoneal, subcutaneous, and intramuscular administration. In certain embodiments, the composition is administered intratumorally or peritumorally. In certain embodiments, the subject is treated with at least one additional anti-cancer agent. In certain embodiments, the anti-cancer agent is selected from the group consisting of paclitaxel, cisplatin, topotecan, gemcitabine, bleomycin, etoposide, carboplatin, docetaxel, doxorubicin, topotecan, cyclophosphamide, trabectedin, olaparib, tamoxifen, letrozole, and bevacizumab. In certain embodiments, the subject is treated with at least one additional anti-cancer therapy. In certain embodiments, the anti-cancer therapy is radiation therapy, chemotherapy, or surgery. In certain embodiments, the cancer is a solid tumor. In certain embodiments, the cancer is selected from the group consisting of breast cancer, ovarian cancer, prostate cancer, pancreatic cancer, lung cancer, liver cancer, throat cancer, stomach cancer, and kidney cancer. In certain embodiments, the cancer is liver cancer. In certain embodiments, the subject is a mammal. In certain embodiments, the mammal is human.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF FIGURES

FIG. 17 depicts a schematic representation of the strategy developed to compete with wild type GAPDH to block its glycolytic reaction. In the presence of ectopically expressed mutant GAPDH (i.e. where the NAD binding is interrupted) the catalysis of substrate (glycerladehyde-3-phosphate) is inhibited. Thus a mutant GAPDH that is functionally impaired yet efficient to compete for substrate-binding competitively inhibits wild type GAPDH.

FIG. 18 contains three panels, (a)-(c), depicting the generation of mutations at specific sites of human GAPDH through site-directed mutagenesis (a) schematic showing the amino acid sites targeted by site-directed mutagenesis. R13Q (referred as mutant 1) and D39E (referred as mutant 2). (b) DNA sequence showing generation of mutation at NAD binding site corresponding to amino acid position 13 indicated by box. Amino acid residue 13, R (arginine) [CGT] is mutated to Q (glutamine) [CAA]. A positively charge amino acid replaced with negatively charged amino acid. (c) DNA sequence showing generation of mutation at non-NAD binding site corresponding to amino acid position 39 indicated by box. Amino acid residue #39 D (aspartic acid) [GAC] is mutated to E, (glutamic acid) [GAA]. A negatively charge amino acid replaced by a different but negatively charged amino acid. Wild refers to normal wild type human GAPDH sequence.

FIG. 20 depicts human GAPDH amino acid sequence showing target mutation sites (in bold) for the generation of R13Q and D39E mutants. Amino acid #13, R (arginine) [CGT] is mutated to Q (glutamine) [CAA] (indicated by bold, italics font). A positively charged amino acid replaced with negatively charged amino acid. Amino acid #39, D (aspartic acid) [GAC] is mutated to E, (glutamic acid) [GAA] (indicated by bold, italics font). A negatively charged amino acid replaced by another negatively charged amino acid.

DETAILED DESCRIPTION OF THE INVENTION

A. Definitions

Figure 1:
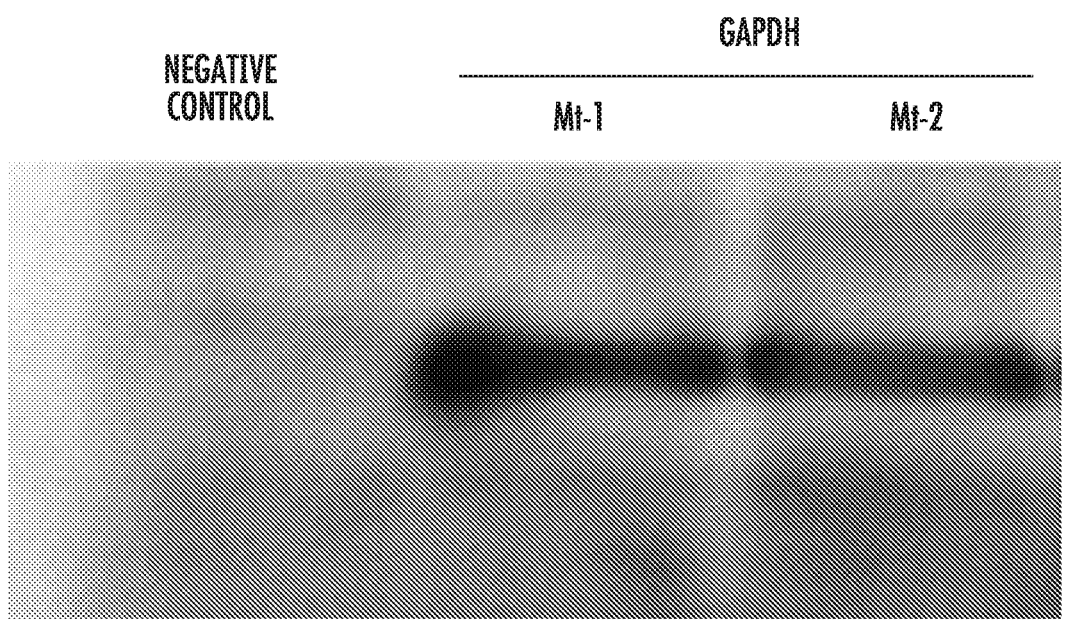
FIG. 1 depicts an immunoblot showing the translation of mutant (mt) GAPDH. Human GAPDH plasmid with a myc-DDK tag was subjected to site directed mutations using the Clontech, mutagenesis kit. Following the confirmation of mutations corresponding to mutant-1 and mutant-2 (FIG. 2) by DNA sequencing, the mutant plasmids were transcribed to mRNA and translated to protein $T_{NT}$ T7 quick coupled transcription/translation system. The translated mutant proteins were subjected to western blot and probed with anti-myc-DDK antibody.

The articles "a" and "an" are used herein to refer to one or to more than one (i.e., to at least one) of the grammatical object of the article. By way of example, "an element" means one element or more than one element.

The term "administering" means providing a pharmaceutical agent or composition to a subject, and includes, but is not limited to, administering by a medical professional and self-administering.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, hepatocellular carcinoma (HCC), acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor.

The term "cirrhosis" means the impairment of liver function caused by fibrotic tissue that reduces the flow of blood through the liver.

The terms "fibrosis" and "liver fibrosis" means the deposition of excess extracellular matrix in the liver.

The term "inhibit" or "inhibits" means to decrease, suppress, attenuate, diminish, arrest, or stabilize the development or progression of a disease, disorder, or condition, the activity of a biological pathway, or a biological activity, such as the growth of a solid malignancy, e.g., by at least 10%, 20%, 30%, 40%, 50%, 60%, 70%, 80%, 90%, 95%, 98%, 99%, or even 100% compared to an untreated control subject, cell, biological pathway, or biological activity or compared to the target, such as a growth of a solid malignancy, in a subject before the subject is treated. By the term "decrease" is meant to inhibit, suppress, attenuate, diminish, arrest, or stabilize a symptom of a cancer disease, disorder, or condition. It will be appreciated that, although not precluded, treating a disease, disorder or condition does not require that the disease, disorder, condition or symptoms associated therewith be completely eliminated.

The term "mt-GAPDH" or "mutant GAPDH", as used herein, refers to glyceraldehyde-3-phosphate dehydrogenase having at least one mutation. Said mt-GAPDH is able to compete with wild type GAPDH to block its glycolytic reaction. In the presence of ectopically expressed mutant GAPDH (i.e. where the NAD binding is interrupted) the catalysis of substrate (glycerladehyde-3-phosphate) is inhibited. Thus a mutant GAPDH that is functionally impaired yet efficient to compete for substrate-binding competitively inhibits wild type GAPDH. In some embodiments, the mt-GAPDH comprise an Arginine to Glutamine mutation at position 13 (referred to herein as "mt-GAPDH-1" or "GAPDH mutant-1"). In some embodiments, the mt-GAPDH comprise an Aspartic Acid to Glutamic Acid mutation at position 39 (referred to herein as "mt-GAPDH-2" or "GAPDH mutant-2").

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic acid addition salts of compounds.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

A "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The term "subject in need thereof" means a subject identified as in need of a therapy or treatment.

The terms "systemic administration," "administered systemically," "peripheral administration," and "administered peripherally" mean the administration of a compound, drug or other material other than directly into the central nervous system, such that it enters the patient's system and, thus, is subject to metabolism and other like processes, for example, subcutaneous administration.

The term "therapeutic agent" or "pharmaceutical agent" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents is known in the art and may be identified by their effects. Certain therapeutic agents are capable of regulating red cell proliferation and differentiation. Examples include chemotherapeutic nucleotides, drugs, hormones, non-specific (e.g. non-antibody) proteins, oligonucleotides (e.g., antisense oligonucleotides that bind to a target nucleic acid sequence (e.g., mRNA sequence)), peptides, and peptidomimetics.

The term "therapeutic effect" refers to a local or systemic effect in animals, particularly mammals, and more particularly humans, caused by a pharmacologically active substance.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The term "treating" a disease in a subject or "treating" a subject having a disease refers to subjecting the subject to a pharmaceutical treatment, e.g., the administration of a drug, such that at least one symptom of the disease is decreased, prevented from worsening, or delayed from worsening.

The terms "tumor," "solid malignancy," or "neoplasm" refer to a lesion that is formed by an abnormal or unregulated growth of cells. Preferably, the tumor is malignant, such as that formed by a cancer.

An "expression vector" or "expression cassette" refers to a nucleic acid construct, which when introduced into a host cell, results in transcription and/or translation of a RNA and/or polypeptide, respectively. The expression cassette may include a nucleic acid comprising a promoter sequence, with or without a sequence containing mRNA polyadenylation signals, and one or more restriction enzyme sites located downstream from the promoter allowing insertion of heterologous gene sequences. The expression cassette is capable of directing the expression of a heterologous protein when the gene encoding the heterologous protein is operably linked to the promoter by insertion into one of the restriction sites. The recombinant expression cassette allows expression of the heterologous protein in a host cell when the expression cassette containing the heterologous protein is introduced into the host cell. Expression cassettes can be derived from a variety of sources depending on the host cell to be used for expression. For example, an expression cassette can contain components derived from a viral, bacterial, insect, plant, or mammalian source. In the case of both expression of transgenes and inhibition of endogenous genes (e.g., by antisense, or sense suppression) the inserted polynucleotide sequence need not be identical and can be "substantially identical" to a sequence of the gene from which it was derived.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g., enhancers) in an expression cassette. Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include nucleic acid sequences that have at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include polypeptide sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

B. mt-GAPDH Compositions

The present invention provides pharmaceutical compositions comprising nucleic acid molecule, polypeptide molecules, or expression constructs comprising mutant GAPDH comprising at least one mutation. Such compositions are referred herein as mt-GAPDH.

In certain embodiments, the mt-GAPDH are derived from SEQ ID NOs: 1 and 2, which corresponds to human wild-type GAPDH. In some embodiments, the nucleic acid sequence of GAPDH is set forth in SEQ ID NO: 1.

```
                                            (SEQ ID NO: 1)
ATGGGGAAGGTGAAGGTCGGAGTCAACGGATTTGGTCGTTTTGGGCGCCT

GGTCACCAGGGCTGCTTTTAACTCTGGTAAAGTGGATATTGTTGCCATCA

ATGACCCCTTCATTGACCTCAACTACATGGTTTACATGTTCCAATATGAT

TCCACCCATGGCAAATTCCATGGCACCGTCAAGGCTGAGAACGGGAAGCT

TGTCATCAATGGAAATCCCATCACCATCTTCCAGGAGCGAGATCCCTCCA

AAATCAAGTGGGGCGATGCTGGCGCTGAGTACGTCGTGGAGTCCACTGGC

GTCTTCACCACCATGGAGAAGGCTGGGGCTCATTTGCAGGGGGGAGCCAA

AAGGGTCATCATCTCTGCCCCCTCTGCTGATGCCCCCATGTTCGTCATGG

GTGTGAACCATGAGAAGTATGACAACAGCCTCAAGATCATCAGCAATGCC

TCCTGGACCACCAACTGGTTAGCACCCCTGGCCAAGGTCATCCATGACAA

CTTTGGTATCGTGGAAGGACTCATGACCACAGTCCTTGCCATCACTGCCA

CCCAGAAGACTGTGGATGGCCCCTCCGGGAAACTGTGGCGTGATGGCCGC

GGGGCTCTCCAGAACATCATCCCTGCCTCTACTGGCGCTGCCAAGGCTGT

GGGCAAGGTCATCCCTGAGCTGAACGGGAAGCTCACTGGCATGGCCTTCC

GTGTCCCCACTGCCAACGTGTCAGTGGTGGACCTGACCTGCCGTCTAGAA

AAACCTGCCAAATATGATGACATCAAGAAGGTGGTGAAGCAGGCGTCGGA

GGGCCCCCTCAAGGGCATCCTGGGCTACACTGAGCACCAGGTGGTCTCCT

CTGACTTCAACAGCGACACCCACTCCTCCACCTTTGACGCTGGGGCTGGC

ATTGCCCTCAACGACCACTTTGTCAAGCTCATTTCCTGGTATGACAAGGA

ATTTGGCTACAGCAACAGGGTGGTGGACCTCATGGCCCACATGGCCTCCA

AGGAGTAA
```

In some embodiments, the polypeptide sequence of GAPDH is set forth in SEQ ID NO: 2.

```
                                            (SEQ ID NO: 2)
M G K V K V G V N G F G R I G R L V T R A A F N S

G K V D I V A I N D P F I D L N Y M V Y M F Q Y D

S T H G K F H G T V K A E N G K L V I N G N P I T

I F Q E R D P S K I K W G D A G A E Y V V E S T G

V F T T M E K A G A H L Q G G A K R V I I S A P S

A D A P M F V M G V N H E K Y D N S L K I I S N A

S C T T N C L A P L A K V I H D N F G I V E G L M

T T V H A I T A T Q K T V D G P S G K L W R D G R

G A L Q N I I P A S T G A A K A V G K V I P E L N

G K L T G M A F R V P T A N V S V V D L T C R L E

K P A K Y D D I K K V V K Q A S E G P L K G I L G

Y T E H Q V V S S D F N S D T H S S T F D A G A G

I A L N D H F V K L I S W Y D N E F G Y S N R V V

D L M A H M A S K E
```

In some embodiments, the GAPDH has at least one mutation in the nucleic acid sequence at positions. Table 1 depicts primer used for the generation of mutant GAPDHs.

TABLE 1

Table 1:

| Primer set | Sequence | Size | TM |
|---|---|---|---|
| NAD mutation R13-14Q forward | 5'TCAACGGATTTGGTCAATTTGGG CGCCTGGTCA3' (SEQ ID: 7) | 33 | 75 |
| NAD mutation R13Q reverse | 5'TGACCAGGCGCCCAAATTGACCAA ATCCGTTGA3' (SEQ ID NO: 8) | 33 | 75 |
| Aspartate mutation D39E forward | 5' AATGACCCCTTCATTAGACTCAA CTACATGGTT3' (SEQ ID NO: 9) | 33 | 67.8 |
| Aspartate mutation D39E reverse | 5' AACCATGTAGTTGAGTCTAATGA AGGGGTCATT3' (SEQ ID NO: 10) | 33 | 67.8 |

In certain embodiments, the mutant GADPH has a nucleic acid sequence comprising a mutation of CGT at positions 37-39 of SEQ ID NO: 1 to CAA. In certain embodiments, the mutant GADPH has a nucleic acid sequence comprising a mutation of GAC at positions 115-117 of SEQ ID NO: 1 to GAA. In certain embodiments, the mutant GADPH has a polypeptide sequence comprising a mutation of Arginine at position 13 of SEQ ID NO: 2 to Glutamine. In certain embodiments, the mutant GADPH has a polypeptide sequence comprising a mutation of Aspartic Acid at position 39 of SEQ ID NO: 2 to Glutamic Acid.

In some embodiments of the compositions and methods provided herein, the mt-GADPH may comprise nucleic acid molecules comprising nucleotide sequences at least 70%, 75%, 80%, 85%, 90%, 91%, 92%, 93%, 94%, 95%, 96%, 97%, 98% or 99% identical to the nucleotide sequence set forth in SEQ ID NO: 3 or 5. In some embodiments of the compositions and methods provided herein, the mt-GADPH has a nucleic acid molecule that consists essentially of the nucleotide set forth in SEQ ID NO: 3 or 5.

In some embodiments of the compositions and methods provided herein, the mt-GADPH may comprise polypeptide molecules comprising amino acid sequences at least 70%, 75%, 80%, 85%, 90%, 91%, 92%, 93%, 94%, 95%, 96%, 97%, 98% or 99% identical to the amino acid sequence set forth in SEQ ID NO: 4 or 6. In some embodiments of the methods provided herein, the mt-GADPH has an amino acid sequence that consists essentially of the amino acid sequence set forth in SEQ ID NO: 4 or 6.

As is well-known to those skilled in the art, polypeptides having substantial sequence similarities can cause identical or very similar immune reaction in a host animal. Accordingly, in some embodiments, a derivative, equivalent, variant, fragment, or mutant of mt-GADPH can also suitable for the methods, compositions and kits provided herein.

In some embodiments, the altered polypeptide may have an altered amino acid sequence, for example by conservative substitution, yet still elicits immune responses which react with the unaltered protein antigen, and are considered functional equivalents. As used herein, the term "conservative substitution" denotes the replacement of an amino acid residue by another, biologically similar residue. It is well known in the art that the amino acids within the same conservative group can typically substitute for one another without substantially affecting the function of a protein. According to certain embodiments, the derivative, equivalents, variants, or mutants of the mt-GADPH are at least 85% homologous to a sequence set forth in SEQ ID NOs: 3, 4, 5, or 6. In some embodiments, the homology is at least 90%, at least 95%, or at least 98%.

In some embodiments the composition comprises an expression vector comprising an open reading frame encoding a mt-GADPH. In some embodiments, the mt-GADPH nucleic acid molecule includes regulatory elements necessary for expression of the open reading frame. Such elements can include, for example, a promoter, an initiation codon, a stop codon, and a polyadenylation signal. In addition, enhancers can be included. These elements can be operably linked to a sequence that encodes the mt-GADPH polypeptide. In some embodiments, the mt-GADPH is linked to a tumor specific promoter. In certain embodiments, the tumor-specific promoter is selected from the group consisting of hTERT, Cholecystokinin A Receptor (CCKAR), and Alpha feto protein (AFP).

In one aspect, the present invention provides pharmaceutically acceptable compositions which comprise a therapeutically-effective amount of one or more such mt-GAPDH described above, formulated together with one or more pharmaceutically acceptable carriers (additives) and/or diluents. In another aspect the compositions can be administered as such or in admixtures with pharmaceutically acceptable carriers and can also be administered in conjunction with other anti-cancer therapies, such as chemotherapeutic agents, scavenger compounds, radiation therapy, biologic therapy, and the like. Conjunctive therapy thus includes sequential, simultaneous and separate, or co-administration of the composition, wherein the therapeutic effects of the first administered has not entirely disappeared when the subsequent compound is administered.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, certain embodiments of the mt-GAPDH compositions may contain a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the mt-GAPDH compositions of the present invention may contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The mt-GAPDH composition formulations include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect.

In certain embodiments, a formulation of mt-GAPDH compositions can comprise other carriers to allow more stability, to allow more stability, different releasing properties in vivo, targeting to a specific site, or any other desired characteristic that will allow more effective delivery of the mt-GAPDH compositions to a subject or a target in a subject, such as, without limitation, liposomes, microspheres, nanospheres, nanoparticles, bubbles, micelle forming agents, e.g., bile acids, and polymeric carriers, e.g., polyesters and polyanhydrides. In certain embodiments, an aforementioned formulation renders orally bioavailable a compound of the present invention.

Liquid dosage formulations of mt-GAPDH compositions include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an active ingredient. A mt-GAPDH composition of the present invention may also be administered as a bolus, electuary or paste.

In solid dosage forms (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical or transdermal administration of a mt-GAPDH composition of the present invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions suitable for parenteral administration can comprise sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In certain embodiments, the above-described pharmaceutical compositions can be combined with other pharmacologically active compounds ("second active agents") known in the art according to the methods and compositions provided herein. Second active agents can be large molecules (e.g., proteins) or small molecules (e.g., synthetic inorganic, organometallic, or organic molecules). In one embodiment, second active agents independently or synergistically help to treat cancer.

For example, chemotherapeutic agents are anti-cancer agents. The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and *vinca* alkaloid natural antineoplastics, such as vinblastine and vincristine.

Further, the following drugs may also be used in combination with an antineoplastic agent, even if not considered antineoplastic agents themselves: dactinomycin; daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons α, β, and γ; hormones, such as luteinizing hormone releasing hormone (LHRH) and analogues and, gonadotropin releasing hormone (GnRH); growth factors, such as transforming growth factor-β (TGF-β), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-α & β (TNF-α & β); invasion inhibiting factor-2 (IIF-2); bone morphogenetic proteins 1-7 (BMP 1-7); somatostatin; thymosin-α-1; γ-globulin; superoxide dismutase (SOD); complement factors; anti-angiogenesis factors; antigenic materials; and prodrugs.

Chemotherapeutic agents for use with the compositions and methods of treatment described herein include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omega1I; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylomithine (DMFO); retinoids such as retinoic acid; capecitabine; and pharmaceutically acceptable salts, acids or derivatives of any of the above.

In another embodiment, the composition of the invention may comprise other biologically active substances, including therapeutic drugs or pro-drugs, for example, other chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Exemplary scavenger compounds include, but are not limited to thiol-containing compounds such as glutathione, thiourea, and cysteine; alcohols such as mannitol, substituted phenols; quinones, substituted phenols, aryl amines and nitro compounds.

Various forms of the chemotherapeutic agents and/or other biologically active agents may be used. These include, without limitation, such forms as uncharged molecules, molecular complexes, salts, ethers, esters, amides, and the like, which are biologically active.

C. Therapeutic Methods

The present invention further provides novel therapeutic methods of preventing, delaying, reducing, and/or treating a cancer, including a cancerous tumor. In one embodiment, a method of treatment comprises administering to a subject (e.g., a subject in need thereof), an effective amount of a mt-GAPDH composition. A subject in need thereof may include, for example, a subject who has been diagnosed with a tumor, including a pre-cancerous tumor, a cancer, or a subject who has been treated, including subjects that have been refractory to the previous treatment.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

The methods of the present invention may be used to treat any cancerous or pre-cancerous tumor. In certain embodiments, the cancerous tumor has a highly glycolytic phenotype. For example, highly glycolytic tumors may be located in a tissue selected from brain, colon, urogenital, lung, renal, prostate, pancreas, liver, esophagus, stomach, hematopoietic, breast, thymus, testis, ovarian, skin, bone marrow and/or uterine tissue. In some embodiments, methods and compositions of the present invention may be used to treat any cancer. Cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The compositions described herein may be delivered by any suitable route of administration, including orally, nasally, transmucosally, ocularly, rectally, intravaginally, parenterally, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The terms "systemic administration," "administered systemically," "peripheral administration," and "administered peripherally" as used herein mean the administration of the mt-GAPDH such that it enters the patient's system and, thus, is subject to metabolism and other like processes.

The terms "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

In certain embodiments the pharmaceutical compositions are delivered generally (e.g., via oral or parenteral administration). In certain other embodiments the pharmaceutical compositions are delivered locally through direct injection into a tumor or direct injection into the tumor's blood supply (e.g., arterial or venous blood supply). In some embodiments, the pharmaceutical compositions are delivered by both a general and a local administration. For example, a subject with a tumor may be treated through direct injection of a composition containing a composition described herein into the tumor or the tumor's blood supply in combination with oral administration of a pharmaceutical composition of the present invention. If both local and general administration is used, local administration can occur before, concurrently with and/or after general administration.

In certain embodiments, the methods of treatment of the present invention, including treating a cancerous or pre-cancerous tumor comprise administering compositions described herein in combination with a second agent and/or therapy to the subject. By "in combination with" is meant the administration of the mt-GAPDH with one or more therapeutic agents either simultaneously, sequentially, or a combination thereof. Therefore, a subject administered a combination of mt-GAPDH and/or therapeutic agents, can receive the mt-GAPDH as described herein, and one or more therapeutic agents at the same time (i.e., simultaneously) or at different times (i.e., sequentially, in either order, on the same day or on different days), so long as the effect of the combination of both agents is achieved in the subject. When administered sequentially, the agents can be administered within 1, 5, 10, 30, 60, 120, 180, 240 mins. or longer of one another. In other embodiments, agents administered sequentially, can be administered within 1, 5, 10, 15, 20 or more days of one another.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times. In such combination therapies, the therapeutic effect of the first administered agent is not diminished by the sequential, simultaneous or separate administration of the subsequent agent(s).

Such methods in certain embodiments comprise administering pharmaceutical compositions comprising compositions described herein in conjunction with one or more chemotherapeutic agents and/or scavenger compounds, including chemotherapeutic agents described herein, as well as other agents known in the art. Conjunctive therapy includes sequential, simultaneous and separate, or co-administration of the composition in a way that the therapeutic effects of the mt-GAPDH administered have not entirely disappeared when the subsequent compound is administered. In one embodiment, the second agent is a chemotherapeutic agent. In another embodiment, the second agent is a scavenger compound. In another embodiment, the second agent is radiation therapy. In a further embodiment, radiation therapy may be administered in addition to the composition. In certain embodiments, the second agent may be co-formulated in the separate pharmaceutical composition.

In some embodiments, the subject pharmaceutical compositions of the present invention will incorporate the substance or substances to be delivered in an amount sufficient to deliver to a patient a therapeutically effective amount of an incorporated therapeutic agent or other material as part of a prophylactic or therapeutic treatment. The desired concentration of the active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Dosage may be based on the amount of the mt-GAPDH composition per kg body weight of the patient. For example, a range of amounts of compositions or compound encapsulated therein are contemplated, including about 0.001, 0.01, 0.1, 0.5, 1, 10, 15, 20, 25, 50, 75, 100, 150, 200 or 250 mg or more of such compositions per kg body weight of the patient. Other amounts will be known to those of skill in the art and readily determined.

In certain embodiments, the dosage of the mt-GAPDH composition will generally be in the range of about 0.001 mg to about 250 mg per kg body weight, specifically in the range of about 50 mg to about 200 mg per kg, and more specifically in the range of about 100 mg to about 200 mg per kg. In one embodiment, the dosage is in the range of about 150 mg to about 250 mg per kg. In another embodiment, the dosage is about 200 mg per kg.

In some embodiments the molar concentration of the mt-GAPDH composition in a pharmaceutical composition will be less than or equal to about 2.5 M, 2.4 M, 2.3 M, 2.2 M, 2.1 M, 2 M, 1.9 M, 1.8 M, 1.7 M, 1.6 M, 1.5 M, 1.4 M, 1.3 M, 1.2 M, 1.1 M, 1 M, 0.9 M, 0.8 M, 0.7 M, 0.6 M, 0.5 M, 0.4 M, 0.3 M or 0.2 M. In some embodiments the concentration of the mt-GAPDH composition will be less than or equal to about 0.10 mg/ml, 0.09 mg/ml, 0.08 mg/ml, 0.07 mg/ml, 0.06 mg/ml, 0.05 mg/ml, 0.04 mg/ml, 0.03 mg/ml or 0.02 mg/ml.

Actual dosage levels of the active ingredients in the compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular therapeutic agent in the formulation employed, or the ester, salt or amide thereof, the route of administration, the time of administration, the rate of excretion or metabolism of the particular therapeutic agent being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained.

As described above, the mt-GAPDH composition may be administered in combination with radiation therapy. An optimized dose of radiation therapy may be given to a subject as a daily dose. Optimized daily doses of radiation therapy may be, for example, from about 0.25 to 0.5 Gy, about 0.5 to 1.0 Gy, about 1.0 to 1.5 Gy, about 1.5 to 2.0 Gy, about 2.0 to 2.5 Gy, and about 2.5 to 3.0 Gy. An exemplary daily dose may be, for example, from about 2.0 to 3.0 Gy. A higher dose of radiation may be administered, for example, if a tumor is resistant to lower doses of radiation. High doses of radiation may reach, for example, 4 Gy. Further, the total dose of radiation administered over the course of treatment may, for example, range from about 50 to 200 Gy. In an exemplary embodiment, the total dose of radiation administered over the course of treatment ranges, for example, from about 50 to 80 Gy. In certain embodiments, a dose of radiation may be given over a time interval of, for example, 1, 2, 3, 4, or 5 mins, wherein the amount of time is dependent on the dose rate of the radiation source.

In certain embodiments, a daily dose of optimized radiation may be administered, for example, 4 or 5 days a week, for approximately 4 to 8 weeks. In an alternate embodiment, a daily dose of optimized radiation may be administered daily seven days a week, for approximately 4 to 8 weeks. In certain embodiments, a daily dose of radiation may be given a single dose. Alternately, a daily dose of radiation may be given as a plurality of doses. In a further embodiment, the optimized dose of radiation may be a higher dose of radiation than can be tolerated by the patient on a daily base. As such, high doses of radiation may be administered to a patient, but in a less frequent dosing regimen.

The types of radiation that may be used in cancer treatment are well known in the art and include electron beams, high-energy photons from a linear accelerator or from radioactive sources such as cobalt or cesium, protons, and neutrons. An exemplary ionizing radiation is an x-ray radiation.

Methods of administering radiation are well known in the art. Exemplary methods include, but are not limited to, external beam radiation, internal beam radiation, and radiopharmaceuticals. In external beam radiation, a linear accelerator is used to deliver high-energy x-rays to the area of the body affected by cancer. Since the source of radiation originates outside of the body, external beam radiation can be used to treat large areas of the body with a uniform dose of radiation. Internal radiation therapy, also known as brachytherapy, involves delivery of a high dose of radiation to a specific site in the body. The two main types of internal radiation therapy include interstitial radiation, wherein a source of radiation is placed in the effected tissue, and intracavity radiation, wherein the source of radiation is placed in an internal body cavity a short distance from the affected area. Radioactive material may also be delivered to tumor cells by attachment to tumor-specific antibodies. The radioactive material used in internal radiation therapy is typically contained in a small capsule, pellet, wire, tube, or implant. In contrast, radiopharmaceuticals are unsealed sources of radiation that may be given orally, intravenously or directly into a body cavity.

Radiation therapy may also include stereotactic surgery or stereotactic radiation therapy, wherein a precise amount of radiation can be delivered to a small tumor area using a linear accelerator or gamma knife and three dimensional conformal radiation therapy (3DCRT), which is a computer assisted therapy to map the location of the tumor prior to radiation treatment.

Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the mt-GAPDH compositions described herein relative to the wt-GAPDH. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the mt-GAPDH compositions described herein relative to wt-GAPDH. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the mt-GAPDH compositions described herein relative to wt-GAPDH. Although compounds that exhibit toxic side effects may be used, care should be taken to design a delivery system that targets the compounds to the desired site in order to reduce side effects.

In some embodiments, the presently disclosed methods produce at least about a 10%, 15%, 20%, 25%, 30%, 35%, 40%, 45%, 50%, 55%, 60%, 65%, 70%, 75%, 80%, 85%, 90%, 95%, or even 100% inhibition of cancer cell growth in an assay.

In any of the above-described methods, the administering of the mt-GAPDH compositions can result in at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy in a subject, compared to the solid malignancy before administration of the mt-GAPDH compositions.

In some embodiments, the therapeutically effective amount of a mt-GAPDH composition is administered prophylactically to prevent a solid malignancy from forming in the subject.

In some embodiments, the subject is human. In other embodiments, the subject is non-human, such as a mammal.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the $IC_{50}$ as determined in cell culture. Such information may be used to more accurately determine useful doses in humans. Levels in plasma may be measured, for example, by high performance liquid chromatography.

EXEMPLIFICATION

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

An objective of our research is to develop an effective therapeutic strategy for the treatment of solid cancers, using the human liver cancer, hepatocellular carcinoma (HCC) as a model. As described herein, a mutant protein (corresponding to the enzyme GAPDH) has been synthesized and tested for its anticancer effects in vitro and in vivo. This mutant-GAPDH expression may be regulated by tumor specific promoters and unlike (shRNA) they do not depend on U6/H1 promoters. This enables us to selectively target cancers with cancer specific promoters (e.g. Alpha feto protein promoter is active in majority of human HCC).

Example 1: Mutant-GAPDH Competitively Inhibits Wild Type GAPDH

Design and generation of mutant GAPDH are described in the reagents developed/methods section.

Cell-Free Competitive Inhibition of Wild Type GAPDH

To test if the mt-GAPDH can compete with wild type GAPDH the plasmids of the mutants were subjected to T7-quick coupled transcription/translation system [T"$_N$"T] (Promega Co., Madison, Wis.) to synthesize corresponding mutant GAPDH proteins. The objective of synthesizing mutant proteins was to test their efficacy in vitro (in cell free system) to compete with wild type human GAPDH during enzyme reaction. The in vitro transcription/translation reaction confirmed that the mutant GAPDH can be successfully expressed (FIG. 1). The electrophoretic resolution of the products of T"$_N$"T reaction followed by immunoblotting for anti-myc-DDK confirmed that the mutant GAPDH are synthesized and successfully translated into a full length protein (FIG. 1). This demonstrated that the mt-GAPDH can be translated into a full-length protein confirming the feasibility of generating a mutant enzyme (FIG. 1).

Figure 2:
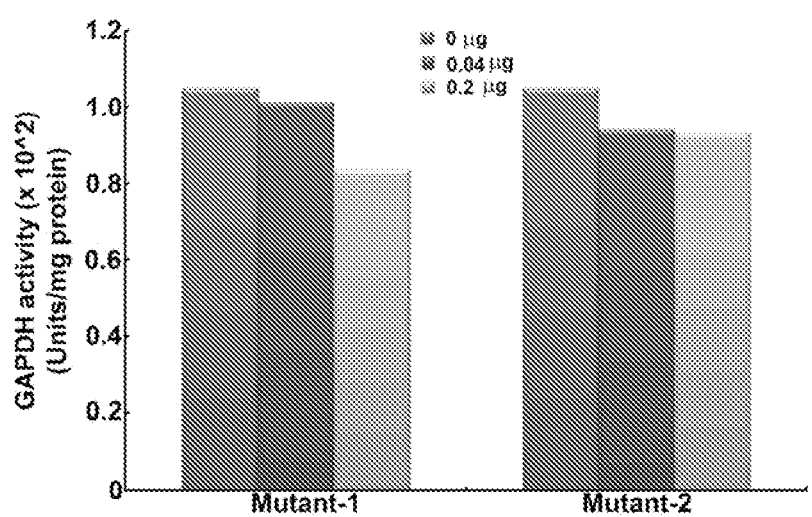
FIG. 2 depicts competitive inhibition of wild type GAPDH by mt-GAPDH. Wild type (rabbit muscle GAPDH) was assayed for its activity as described [8] in the presence or absence of mt-GAPDH synthesized by $T_{NT}$ T in vitro transcription/translation system (FIG. 8). A negative control from the transcription/translation reaction was used for the background signal/noise optimization. A dose-dependent increase in competition was observed. Notably there was a difference in the level of competition between the two mutants.

Next, the mt-GAPDHs thus synthesized were tested for their competitive capacity to inhibit the function of wild type GAPDH. Wild type (rabbit muscle GAPDH) was assayed for its activity as described (8) in the presence or absence of mt-GAPDH synthesized by T"$_N$"T in vitro transcription/translation system (FIG. 1). A negative control from the transcription/translation reaction was used for the background signal/noise optimization. A dose-dependent increase in competition was observed. Notably there was a difference in the level of competition between the two mutants. Data from functional analysis of mt-GAPDH enzyme analysis showed that mutant proteins synthesized by T"$_N$"T coupled in vitro transcription/translation system remarkably competed with wild type GAPDH (FIG. 2). The data also demonstrated that different mutants could have different level of competition implying the necessity to screen for the most efficient inhibitor (mt-GAPDH) (FIG. 2).

Example 2: Mutant GAPDH Affects Cancer Cell Viability

Figure 3:
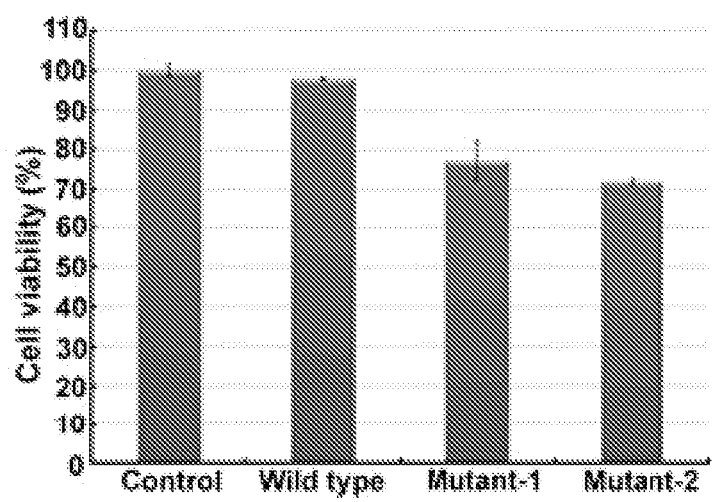
FIG. 3 depicts that mt-GAPDH affects cell viability. Human HCC cell line Huh7 was seeded in a 96-well plate and transfected with wild type and mt-GAPDH and assayed for cell viability after 96 hours. Cell viability was assayed as described.[17] Data shown are mean±SE of triplicates.

Next we investigated if the competition by mt-GAPDH can affect cell viability. A transient transfection of mt-GAPDH using the Turbofectin reagent in human HCC cell line H7 demonstrated that mutant GAPDH significantly reduced cell viability (FIG. 3). This showed that the competitive inhibition achieved in cell-free system (enzyme assay—FIG. 2) is reproducible in cellular system as well. To further validate if the intracellular competition using mt-GAPDH can affect human HCC growth and proliferation we performed colony suppression assay.

Effect of Mt-GAPDH on Colony Formation

Figure 4:
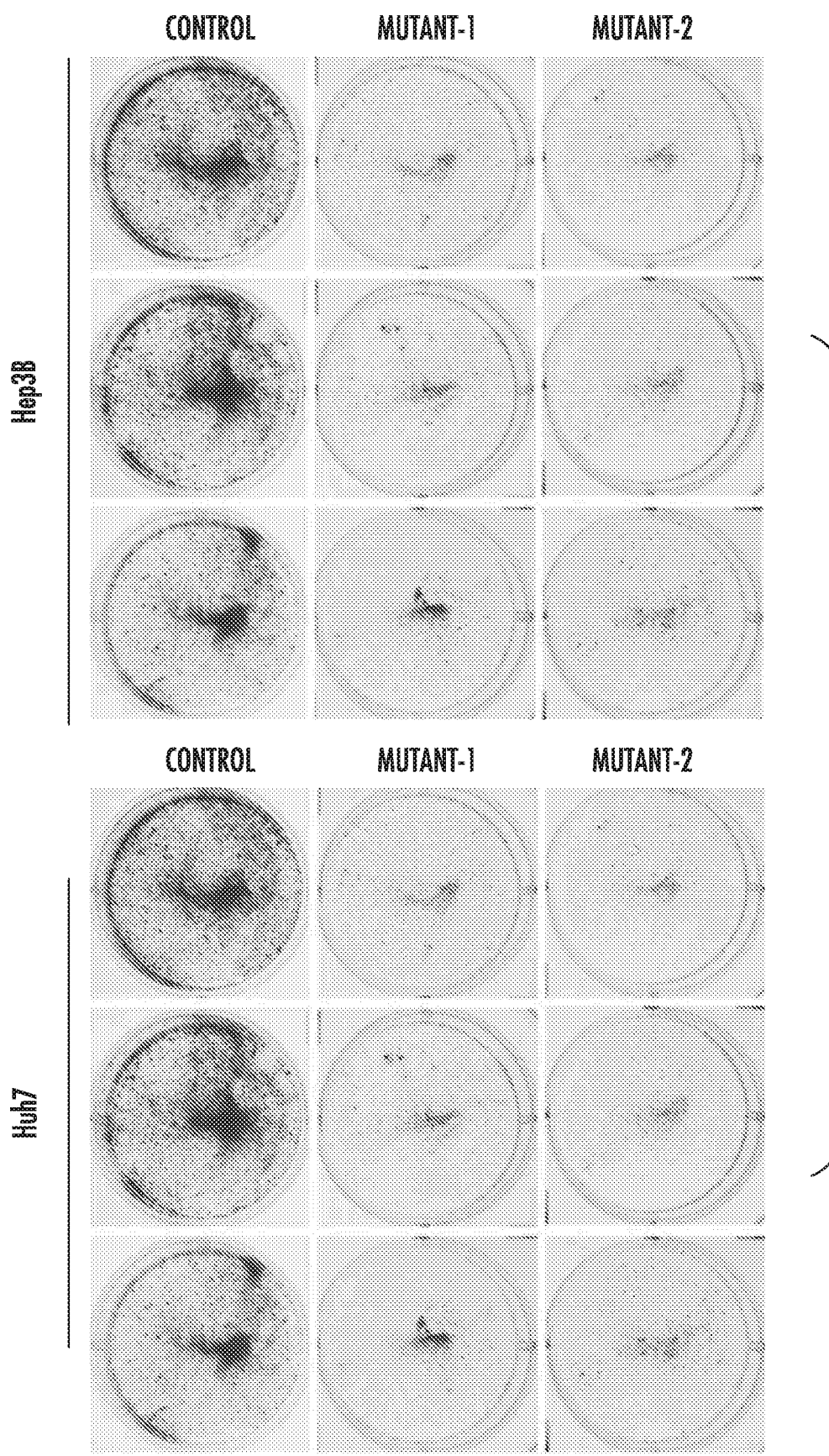
FIG. 4 depicts that mt-GAPDH suppresses colony formation. To test the hypothesis if mt-GAPDH will affect cancer cell growth, the colony suppression assay was performed. Empty vector served as the control. A representative from five replicates is shown.

Human HCC cell lines, Hep3B and Huh7 were transfected with mt-GAPDH and the cells were allowed to grow in 6-well plates, Cell growth and colonies were visualized by crystal violet staining as described (9). As illustrated in FIG. 4, compared to the control (vector) the mutant GAPDH transfected cells showed reduced cell growth and colonies. Representative images from multiple replicates are shown (FIG. 4).

Example 3: Mutant-GAPDH Blocks Tumor Progression in an Animal Model

Figure 5:
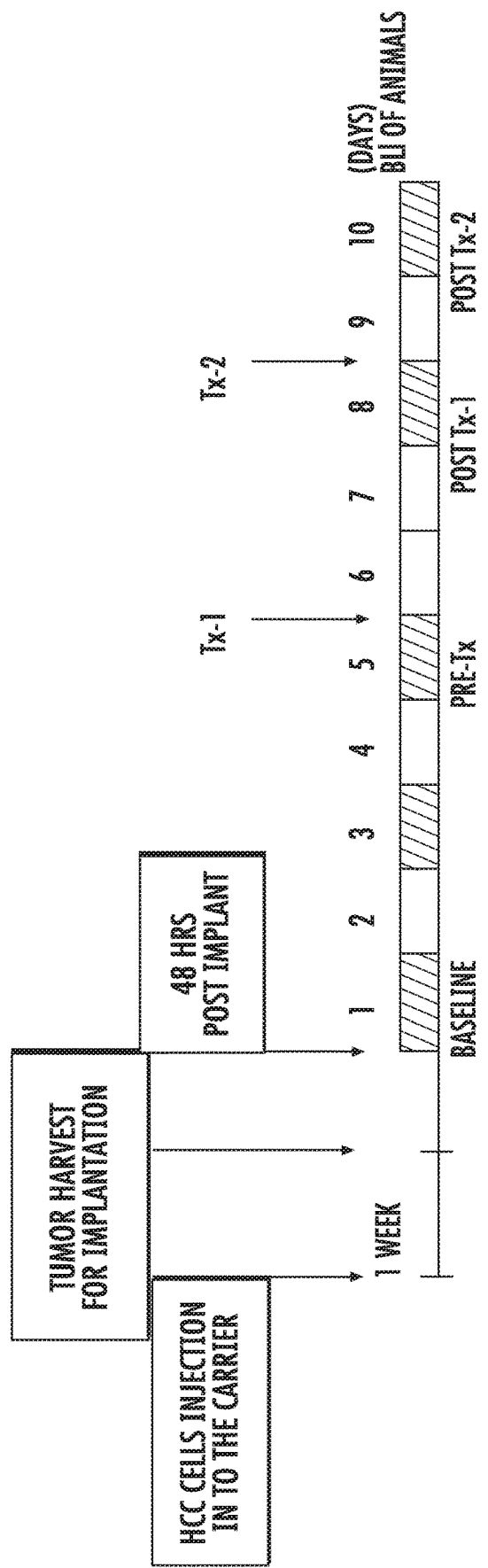
FIG. 5 depicts a schematic showing the design of animal experiments.

The in vivo validation of mt-GAPDH's effectiveness in the inhibition of glycolysis is critical to evaluate the translational potential of this anti-glycolytic, anti-GAPDH strategy. Hence we tested the in vivo efficacy of mt-GAPDH using human HCC tumor model. A schematic of the design of animal experiment is shown in FIG. 5. Animal studies were performed as approved by the Johns Hopkins University Animal Care and Use Committee. For the in vivo experiments, 6-8-week-old male athymic nude mice (body weight, 25-30 g) were used (Crl:NU-Foxn1nu strain; Charles River Laboratory, Germantown, Md.). Tumor xenografts were initiated in male athymic nude mice with subcutaneous injection of luc-Hep3B cells (4-5×10$^6$ cells) growing in log phase. These mice served as donors, and tumors with a positive signal for bioluminescence were extracted, minced into approximately 1 mm$^3$, and implanted subcutaneously into the left bottom flank of experimental mice for further studies. Tumor growth in mice were monitored by BLI, and a baseline signal (on day 1) followed by tumor growth signal (day 5) were recorded. On day 5, the first treatment (Tx-1) was initiated by injecting mutant GAPDH. BLI were recorded on day 8 followed by second treatment (Tx-2). Final BLI were recorded on day 10. Based on the cell viability assay and colony suppression assay data (FIGS. 3 & 4 respectively), the mutant-1 plasmid (mt-1 GAPDH) was used in the animal studies. In brief, mt-GAPDH plasmid was mixed with Turbofectin (for in vivo application) and delivered to the tumor via intratumoral injection. Since these plasmids were still under validation for their functional efficiency in animal model the plasmids were not constructed under AFP-promoter. Due to the lack of AFP-promoter the plasmid was injected subcutaneously into the tumor. For control, an empty vector of the mutant GAPDH was used and delivered as same as the mt-GAPDH plasmid.

BLI protocol: Just before imaging, mice were injected with D-luciferin intraperitoneally (150 mg per kilogram of body weight). Followed by the luciferin injection mice were anesthetized for imaging studies with a gas mixture of 5% isoflurane in 95% oxygen and the anesthesia will be maintained with 2.5% isoflurane via a nose cone. Bioluminescent images were acquired by using a small animal imaging system (IVIS 200; Xenogen).

Mutant-GAPDH Affects Tumor Viability In Vivo

Figure 6:
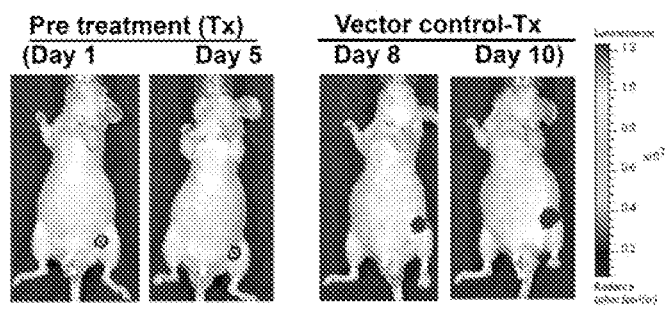
FIG. 6 depicts Luc-Hep3B tumor showing tumor growth and viability unaffected by vehicle control (empty vector).
Figure 7:
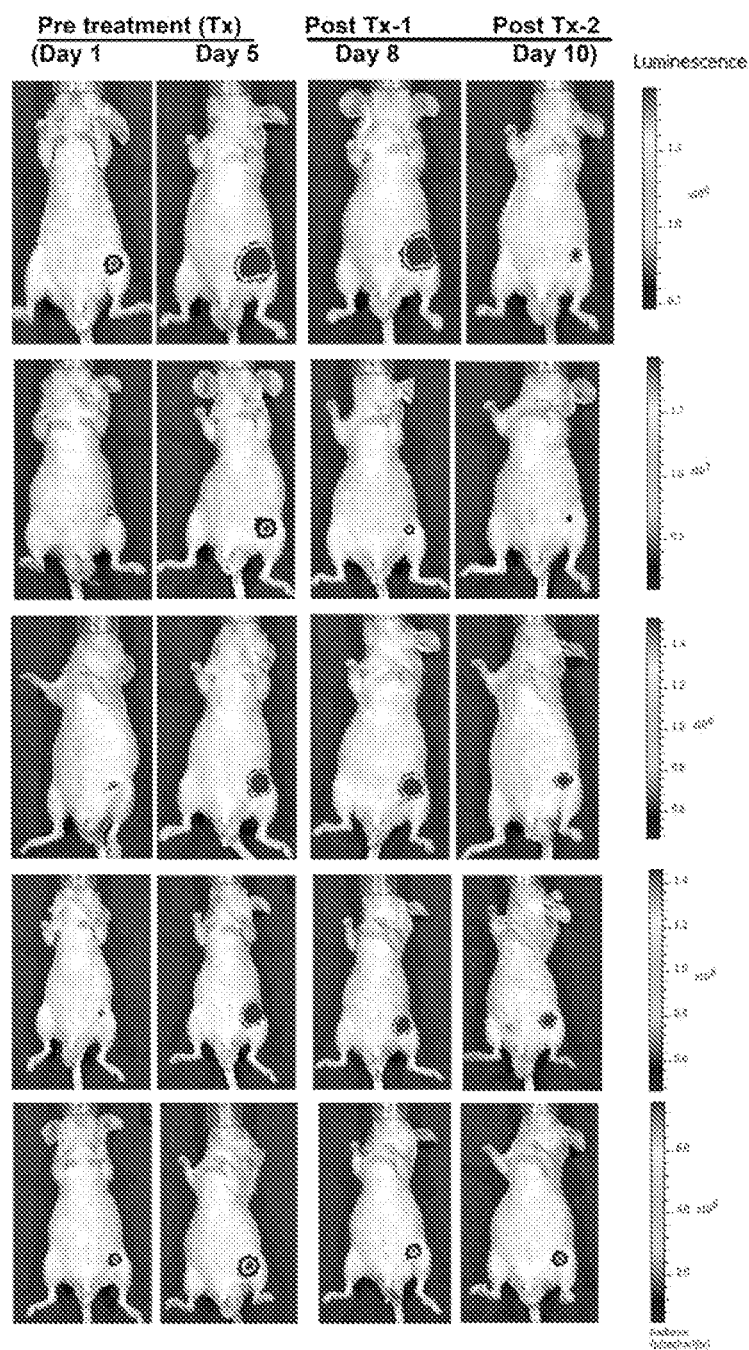
FIG. 7 depicts that Mt-GAPDH shows anticancer effects in vivo. Luc-Hep3B tumors treated with mt-GAPDH showed a marked decrease in tumor growth within two cycles of treatment.
Figure 8:
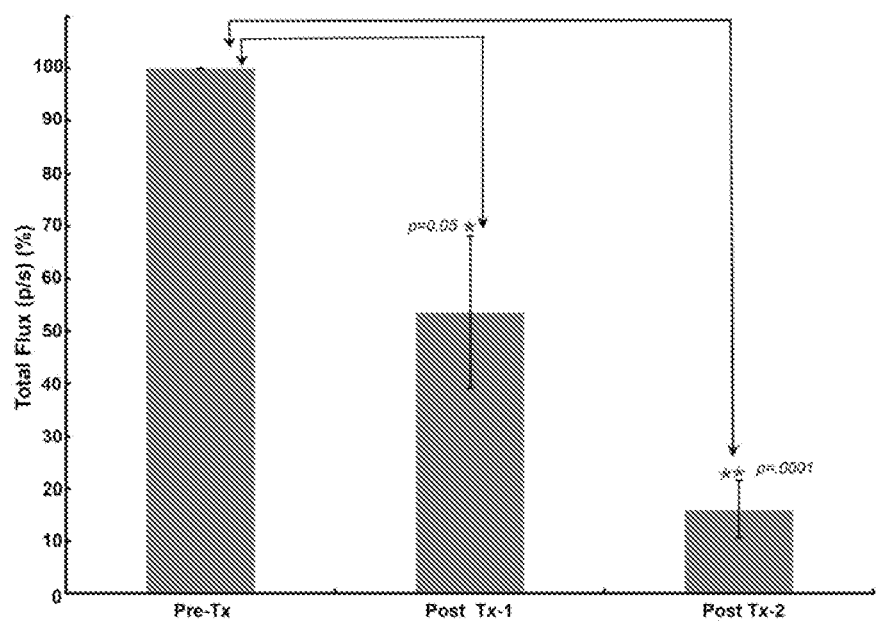
FIG. 8 depicts a graphical representation of the quantitative analysis of BLI intensities of luc-Hep3B tumors before and after treatment with mt-GAPDH.

FIG. 6 shows the BLI signal intensity of luc-Hep3B tumor treated with control vector (vehicle). The tumor growth was unaffected by the empty vector that has no mutant GAPDH. However, as evident from FIG. 7 Luc-Hep3B tumor which showed an increase in growth prior to treatment (Pre-Tx) demonstrated a marked response to the treatment with mutant GAPDH. Quantitative analysis of the BLI signal intensities from animals treated with mt-GAPDH showed a significant tumor response between pre-treatment (Pre-Tx) and post-treatment of tumors with a high level of significance after second cycle of treatment [Post Tx-2] (FIG. 8). Together, the BLI data and the quantitative analysis of total flux established that mt-GAPDH affects human HCC viability in vivo.

Figure 9:
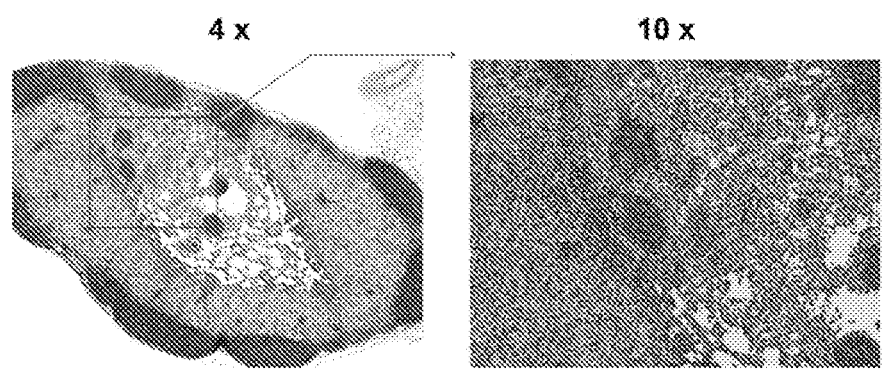
FIG. 9 depicts H&E staining of mt-GAPDH treated Hep3B tumor. Left panel shows the whole tumor section with necrotic center (4×) and the right panel shows a magnified (10×) section of the region (indicated by red square box).

Histopathology:

With the demonstration of significant reduction in tumor viability upon treatment with mutant GAPDH (as evident by animal imaging) we next investigated if the histopathology confirmed tumor cell death. Hematoxylin and Eosin (H&E) staining of tumor sections from treated tumors showed induction of cell death in mt-GAPDH treated animal (FIG. 9).

Example 4: Site Directed Mutations in the Recombinant GAPDH (Used for Ectopic Expression Studies) Did not Affect its Protein Expression in Human HCC Cell Lines Although we have provided the DNA sequence corresponding to the mutated sites, it is imperative to demonstrate that the mutant GAPDH indeed is expressed as full length protein. Also, in order to establish that the full length but mutant-form of GAPDH is the competitive inhibitor and not the ectopic expression of wild type GAPDH, it is critical to show the ectopic expression of full length wild type as well as the mutant GAPDH.

Figure 22:
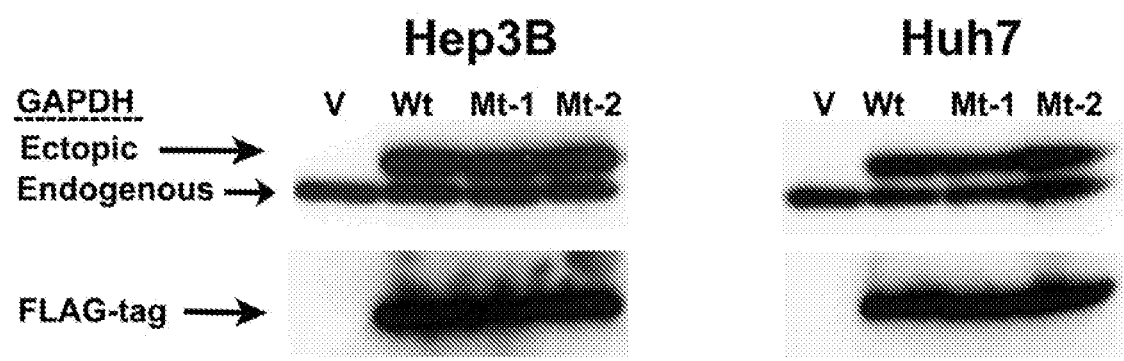
FIG. 22 depicts an immunoblot showing the expression of recombinant GAPDH used for the ectopic expression experiments in human HCC cell lines Hep3B and Huh7. The MYC-DDK tag used in the plasmids contributes for the increase in molecular mass of the ectopic expression that distinguishes it from endogenous, cellular GAPDH. V—vector backbone used as control, Wt—Wild type; Mt-1 Mutant-1 that corresponds to R13Q; Mt-2—Mutant-2 that corresponds to D39E.

Experimentally, the recombinant MYC-DDK-tagged GAPDH corresponding to wild type (Wt) was procured from Origene Technologies. The specific mutations such as R13Q (Mt-1) and D39E (Mt-2) were introduced by site directed mutagenesis (as described before), and verified by DNA sequencing. The MYC-DDK sequence enabled us to distinguish the recombinant, ectopic GAPDH from the endogenous, cellular GAPDH. Also the addition of MYC-DDK tag resulted in an increase in the molecular mass which also facilitated the distinction of ectopic GAPDH from endogenous, cellular GAPDH. Immunoblots were performed using anti-GAPDH antibody as described (Kunjithapatham et al. 2015). A myc-DDK-specific antibody obtained from Origene Technologies was used for myc-DDK-detection in the corresponding immunoblot. FIG. 22 provides evidence for the efficient expression of mutant GAPDH, and the proof that the mutants retain GAPDH epitope as recognized by GAPDH-specific antibody.

Exhibit 5: Hypoxic Cells are Sensitive to Mutant (mt)-GAPDH-Dependent Competitive Inhibition Solid malignancies in general exhibit a hypoxic center (core) and have been known to be resistance to therapeutics. Furthermore such, hypoxic cancer cells rely glycolysis rather than mitochondrial, oxidative phosphorylation. GAPDH, a key enzyme required for glucose metabolism catalyzes the glycolytic reaction of conversion of glyceraldehyde-3-phosphate into 1,3-biphosphoglycerate. If ectopic expression of mutant GAPDH competitively inhibits cellular GAPDH then it is intriguing to investigate if such competition will be effective against hypoxic cancer cells. Note, hypoxic cancer cells have elevated glycolysis by up-regulation of glycolytic enzymes, hence they remain insensitive or resist antiglycolytic therapeutic like 2-deoxyglucose (Maher et al. 2007). Thus, any strategy that can adversely impact tumor glycolysis is a desirable strategy and likely to be a viable therapeutic approach. Hence this study investigated if mutant GAPDH can affect hypoxic cancer cells. Experimentally, following transfection (24 hrs post transfection) Hep3B cells were subjected to hypoxia. The hypoxic condition was performed as described (Mikhaylova et al. 2008). In brief, a hypoxia incubator chamber with 1% of 02 and 5% of CO2 with 37° C. and 90% humidity was used for these experiments. Before the experiment, the chamber was calibrated, and the level of oxygen was maintained using a gas oxygen controller (PROX Model-110; Bio-Spherix, Ltd, Redfield, N.Y.). Cells without plasmid transfection were used as negative controls. Cell viability was assayed using the CellTiter 96 AQueous One Cell Proliferation Assay kit (Promega Corp.). The transfected (+) and non-transfected (−) cells were compared along with vector control (Control), and wild type (ectopic expression of wild type GAPDH).

Figure 23:
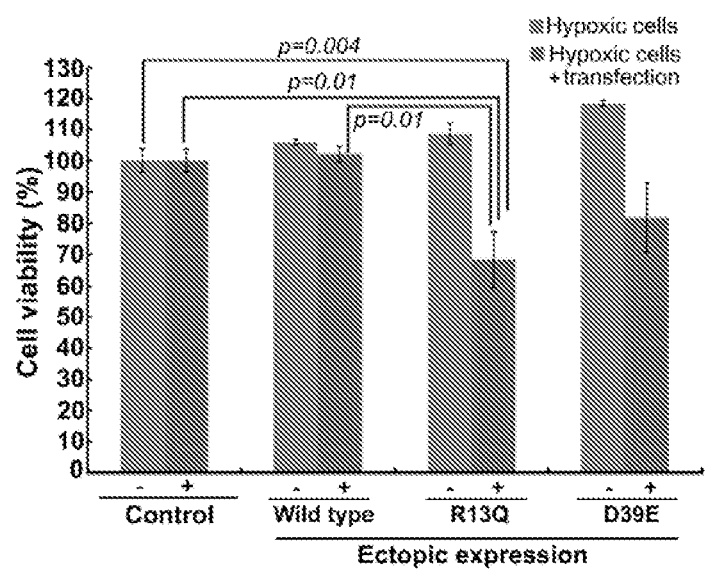
FIG. 23 depicts an ectopic expression of mutant-GAPDH affects cell viability of hypoxic cancer cells. Human HCC cell line Hep3B transfected with mutant GAPDH (R13Q) showed a marked reduction in cell viability compared to other plasmids as well as non-transfected cells. Data shown are mean±SE of triplicates.

In general, hypoxic cancer cells demonstrate resistance to majority of therapies. Furthermore, hypoxic cancers exhibit elevated glycolysis hence are insensitive or resistant to therapeutics that target tumor glycolysis or glucose metabolism (e.g. 2-Deoxyglucose) (Maher et al. 2007). Surprisingly, mutant-GAPDH-dependent inhibition of cellular GAPDH (hence the inhibition of glycolysis) affected the viability of hypoxic cancer cells. In other words, the aggressive or resistant phenotype like hypoxic cancer are sensitive to mutant-GAPDH dependent therapeutic targeting (FIG. 23).

Example 6: Ectopic Expression of Mutant GAPDH Competitively Inhibits Cellular GAPDH in Human HCC To test if the mutant GAPDH dependent anticancer effects such as colony suppression (in vitro) or tumor viability (in vivo) were due to competitive inhibition of cellular GAPDH, GAPDH enzyme activity assay was performed as described (Ganapathy-Kanniappan et al. 2012, Kunjithapatham et al. 2015). In brief, 48 hours post-transfection with respective plasmids, protein samples from Hep3B and Huh7 cells were prepared in ice-cold phosphate buffered saline. The samples were used for the enzyme analysis on the same day of preparation. Spectrophotometric determination of the change in optical density due to a decrease in NADH (during the conversion of 1,3-biphosphoglycerate into glyceraldehyde-3 phosphate) was performed. Protein content was quantified using the Pierce BCA Protein Assay kit (Thermo Fisher Inc.). Enzyme activities were recorded at multiple time intervals (1 min, 2 min, 3 min, 4 min and 5 min), and finally expressed units/mg protein/min. Results were obtained using triplicate experiments. Statistical analysis was performed using Students t-test.

Figure 24:
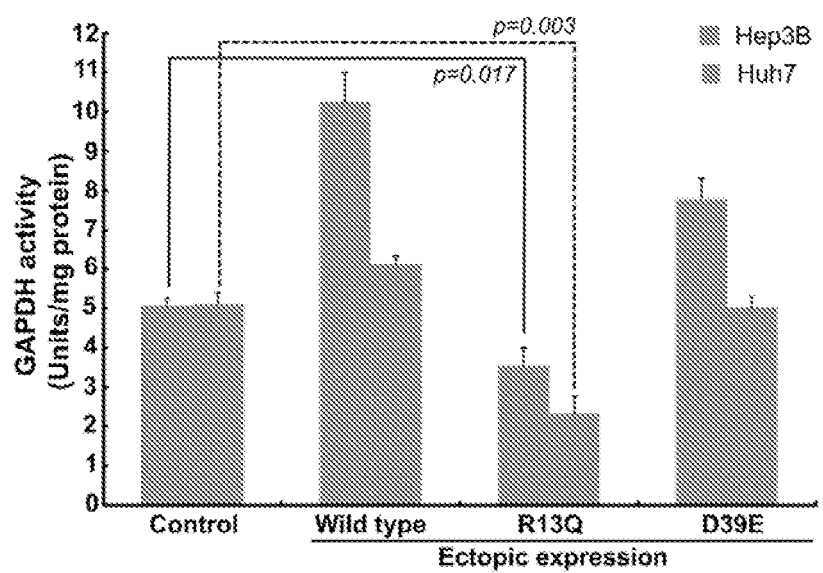
FIG. 24 depicts Human HCC cell lines transfected with mutant (mt)-GAPDH decreases enzymatic function of endogenous-GAPDH. The ectopic expression of mutant GAPDH, particularly the R13Q competitively inhibits endogenous GAPDH in both human HCC cell lines. The ectopic expression of Wild type GPADH that has correspondingly increased the overall activity is used as a positive control. The enzyme activity demonstrates R13Q mutant GAPDH competes with cellular GAPDH during the catalytic reaction. Control refers to vector control (negative control). Data shown are mean±SE of triplicates.

Until now there is no evidence or indication that a mutant enzyme (e.g. GAPDH) could compete with wild type and inhibit its specific enzymatic function (i.e. catalytic reaction). Also it is unknown whether such a strategy can be exploited to target tumor glycolysis to promote anticancer effects. Data shown in FIG. 24 provides the hitherto unknown evidence that mutant GAPDH competitively inhibits cellular GAPDH in cancer as demonstrated in at least two human HCC cell lines.

Example 7: Competitive Inhibition with Mutant-GAPDH Reduces Level of Intracellular ATP in Cancer Cells Intracellular ATP is a critical determinant of cell growth and development. Glucose metabolism is a the primary course of ATP production, and in cancer cells the glycolyit cphenotype plays a major role in ATP synthesis. If glycolysis is disrupted in a glycolytically-addicted cancer cell it would impact the absolute level of intracellular ATP. Unless compensated by other ATP generating mechanisms, the depletion of intracellular ATP could eventually affect cell physiology and lead to cell death. As our findings have indicated that ectopic expression of mutant-GAPDH affects cell viability both in normoxic as well cancer cells, here we investigated if the mutant GAPDH dependent cell death is associated with a change in intracellular ATP.

Figure 25:
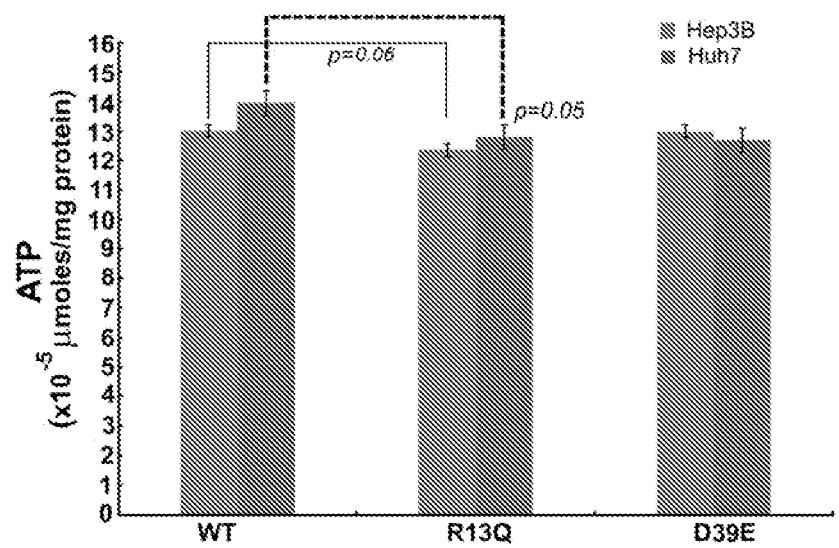
FIG. 25 depicts competitive inhibition by mutant-GAPDH depleting the level of intracellular ATP in human HCC cell lines. The mutant R13Q showed a significant reduction in the absolute level of intracellular ATP. Data shown are mean±SE of triplicates.

Experimentally, human HCC cell lines Hpe3B and Huh7 were subjected to absolute quantification of intracellular ATP 48 hours post-transfection. Cellular ATP was quantifed using CellTiterGlo Luminescent Assay kit (Promega Inc.,) as described (Ganapathy-Kanniappan et al. 2012). A standard graph established using ATP obtained from Sigma Chemical Co.,) was use for the estimation of absolute level of cellular ATP. Evidence that mutant-GAPDH dependent competitive inhibition of cellular GAPDH in cancer results in reduced level of intracellular ATP (i.e.) the absolute quantity of cellular ATP decreased significantly by mutant-GAPDH mediated inhibition of glycolysis (FIG. 25).

Example 8: DN-1: GAPDH Fragment (Truncated) Generated to Test if it has any Inhibitory Function As the mutant GAPDH showed effective competition with the cellular GAPDH it is imperative to ascertain if the full length mutant GAPDH is required for the inhibitory function, or a small fragment such as the truncated GAPDH is sufficient to exert the competitive inhibition. An approach similar to the dominant negative (DN) principle.

To generate the DN-1 GAPDH, the aminoacid (aa) sequence that corresponds to the region between 144 aa to 215 aa were chosen, as this peptide region encompasses the cysteine residues of the catalytic site (152aa and 156 aa). Required start codon with Kozak sequences and stop codon were added to induce the expression. See FIG. 27.

DNA bp 603 TO 819 (size 216 bp)
(SEQ ID NO: 25)
CTCAAGATCATCAGCAATGCCTCCTGCACCACCAACTGCTTAGCACCCCT

GGCCAAGGTCATCCATGACAACTTTGGTATCGTGGAAGGACTCATGACCA

CAGTCCATGCCATCACTGCCACCCAGAAGACTGTGGATGGCCCCTCCGGG

AAACTGTGGCGTGATGGCCGCGGGGCTCTCCAGAACATCATCCCTGCCTC

TACTGGCGCTGCCAAG

Amino acid sequence (size 72 amino acids)
(SEQ ID NO: 26)
LKIISNASCTTNCLAPLAKVIHDNFGIVEGLMTTVHAITATQKTVDGPSG

KLWRDGRGALQNIIPASTGAAK

The start codon (atg) and stop codon (taa) included are shown (indicated in lower case) to indicate the orientation. The cysteine residues (in bold and underlined font) correspond to 152 and 156 aa.

Example 9: DN-2: Another GAPDH Fragment (Truncated) Generated to Test if it has any Inhibitory Function As the mutant GAPDH showed effective competition with the cellular GAPDH it is imperative to ascertain if the full length mutant GAPDH is required for the inhibitory function, or a small fragment such as the truncated GAPDH is sufficient to exert the competitive inhibition. An approach similar to the dominant negative (DN) principle.

To generate the DN-2 GAPDH, the aminoacid sequence that corresponds to the region between 144 aa to 247aa were chosen, as this peptide region encompasses the cysteine residues of the catalytic site (152aa and 156 aa) as well as the additional cysteine residue that is located beyond the catalytic site. Required start codon with Kozak sequences and stop codon were added to induce the expression. See FIG. 27.

DNA bp 603 TO 915 (size 312 bp)
(SEQ ID NO: 27)
CTCAAGATCATCAGCAATGCCTCCTGCACCACCAACTGCTTAGCACCCCT

GGCCAAGGTCATCCATGACAACTTTGGTATCGTGGAAGGACTCATGACCA

CAGTCCATGCCATCACTGCCACCCAGAAGACTGTGGATGGCCCCTCCGGG

AAACTGTGGCGTGATGGCCGCGGGGCTCTCCAGAACATCATCCCTGCCTC

TACTGGCGCTGCCAAGGCTGTGGGCAAGGTCATCCCTGAGCTGAACGGGA

AGCTCACTGGCATGGCCTTCCGTGTCCCCACTGCCAACGTGTCAGTGGTG

GACCTGACCTGC

Amino acid sequence (size 104 amino acids)
(SEQ ID NO: 28)
LKIISNASCTTNCLAPLAKVIHDNFGIVEGLMTTVHAITATQKTVDGPSG

KLWRDGRGALQNIIPASTGAAKAVGKVIPELDGKLTGMAFRVPTANVSVV

DLTC

The start codon (atg) and stop codon (taa) included are shown (indicated in lower case) to indicate the orientation. The cysteine residues (in red font) correspond to 152, 156 and a247 aa.

Example 10: Mutant GAPDH but not the Truncated, Dominant Negative (Fragments) GAPDH Interferes with Glucose Metabolism in Human HCC Cell Line, Hep3B Cancer cells take up glucose vividly, and this phenomenon is very common and frequent in majority, if not all cancers (Gambhir. 2002). Since any adverse effect on glycolysis directly impacts the rate of glucose uptake due to the "feedback inhibition" assessment of glucose uptake will demonstrate the rate of glucose metabolism.

Experimentally, human HCC cell line Hep3B was subjected to glucose uptake measurement using the radiolabeled, $^3$H-2-deoxyglucose (DOG) as the substrate as described (Tan et al. 2010). In brief, 48 hours post transfection with respective plasmids cells were subjected to glucose uptake and the intracellular $^3$H-2-DOG was measured using the scintillation counter. Appropriate negative control was included by using Cytochalasin B to eliminate nonspecific glucose uptake.

Figure 26:
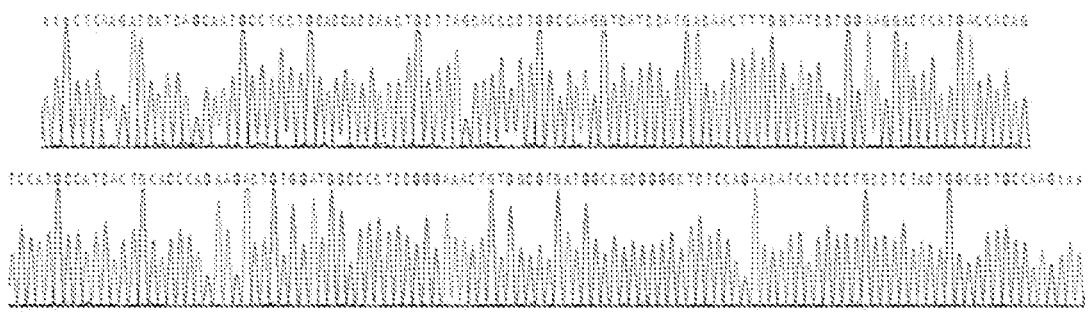
FIG. 26 depicts the GAPDH sequence (SEQ ID NO: 19) encompassing the catalytic site with additional atg at the beginning (start codon) and taa (stop codon) at the end.
Figure 27:
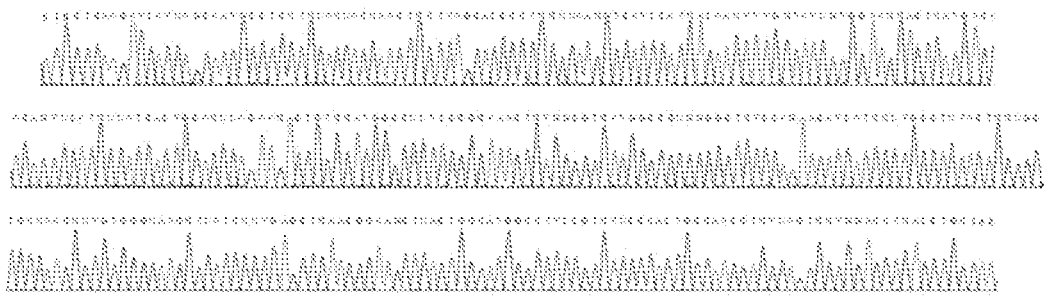
FIG. 27 depicts the GAPDH sequence (SEQ ID NO:20) encompassing all the cysteine residues located within and beyond the catalytic site. The additional atg at the beginning (start codon) and taa (stop codon) at the end are also indicated.
Figure 28:
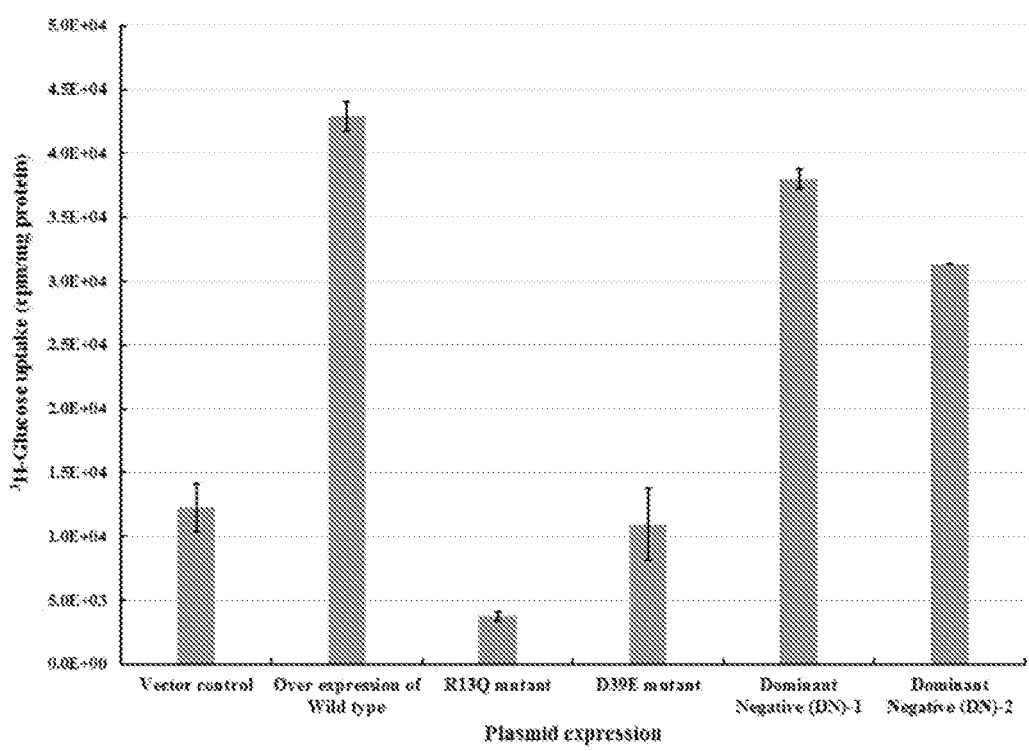
FIG. 28 depicts a $^3$H-glucose uptake assay showing that mutant GAPDH but not truncated, dominant negative (DN) GAPDH affects glucose uptake indicating the impairment of glycolysis by mutant GAPDH. Note: Compare the rate of glucose uptake between vector control and the mutants and DN. Evidently, mutant R13Q reduces the glucose uptake. The wild type (overexpression) was used as positive control which showed increased rate of glucose uptake. Interestingly, both the DN forms of GAPDH have increased the rate of glucose uptake and the cause for which remains unknown.

The competitive inhibition by mutant GAPDH (R13Q) is unexpected and is not imitated or mimicked by other forms of truncated GAPDH or fragments of GAPDH protein. This has been verified by testing two forms of truncated GAPDH, named as dominant negative-1 (DN-1) and dominant negative 2 (DN-2). FIGS. 26 and 27 correspond to the DNA sequence of DN-1 and DN-2 which represent partial protein sequence of GAPDH. DN-1 has peptide region corresponding to amino acids 144 to 215 whereas DN-2 consists of the GAPDH peptide region between amino acids 144 and 247. Both the DN forms encompass the catalytic domain of GAPDH that is responsible for enzymatic reaction. Surprisingly, as evident by FIG. 28, only the R13Q mutant GAPDH affects glucose metabolism in cancer cells but not the two truncated mutant forms (DN-1 and DN-2). Note: The R13Q mutant is a full length GAPDH with site-directed mutation and not a truncated GAPDH.

Reagents Developed/Materials and Methods

AFP-Promoter Driven Expression of Gene of Interest is Feasible

In order to develop an AFP-promoter driven expression of a gene of interest the efficacy and feasibility of AFP-promoter dependent expression needs to be validated. Hence we tested the expression of enhanced green fluorescent protein (eGFP) experimentally cloned under the AFP-promoter. To confirm the expression of eGFP by AFP-promoter, we chose human HCC cell lines that are positive for AFP protein which indicated the presence of functionally active AFP-promoter. The human HCC cell lines tested to analyze the AFP-promoter dependent expression of eGFP are Hep3B, HepG2 and Huh7.

Figure 10:
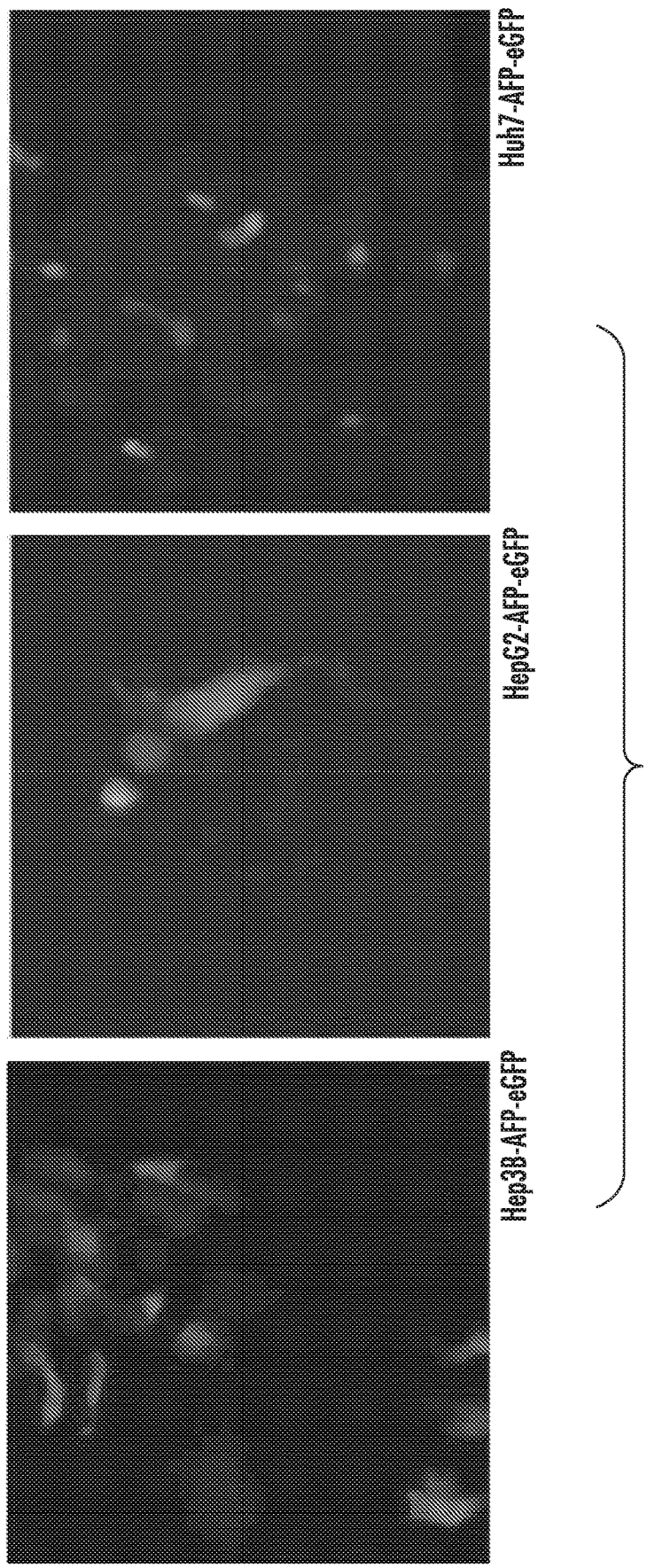
FIG. 10 depicts fluorescent microscopic images of AFP-promoter driven transient expression of eGFP in human HCC cell lines. AFP-promoter dependent ectopic expression of a specific protein (e.g. eGFP) is feasible. In the proposed research we would adopt a similar approach for the ectopic expression of antisense-GAPDH under the control of AFP-promoter.
Figure 11:
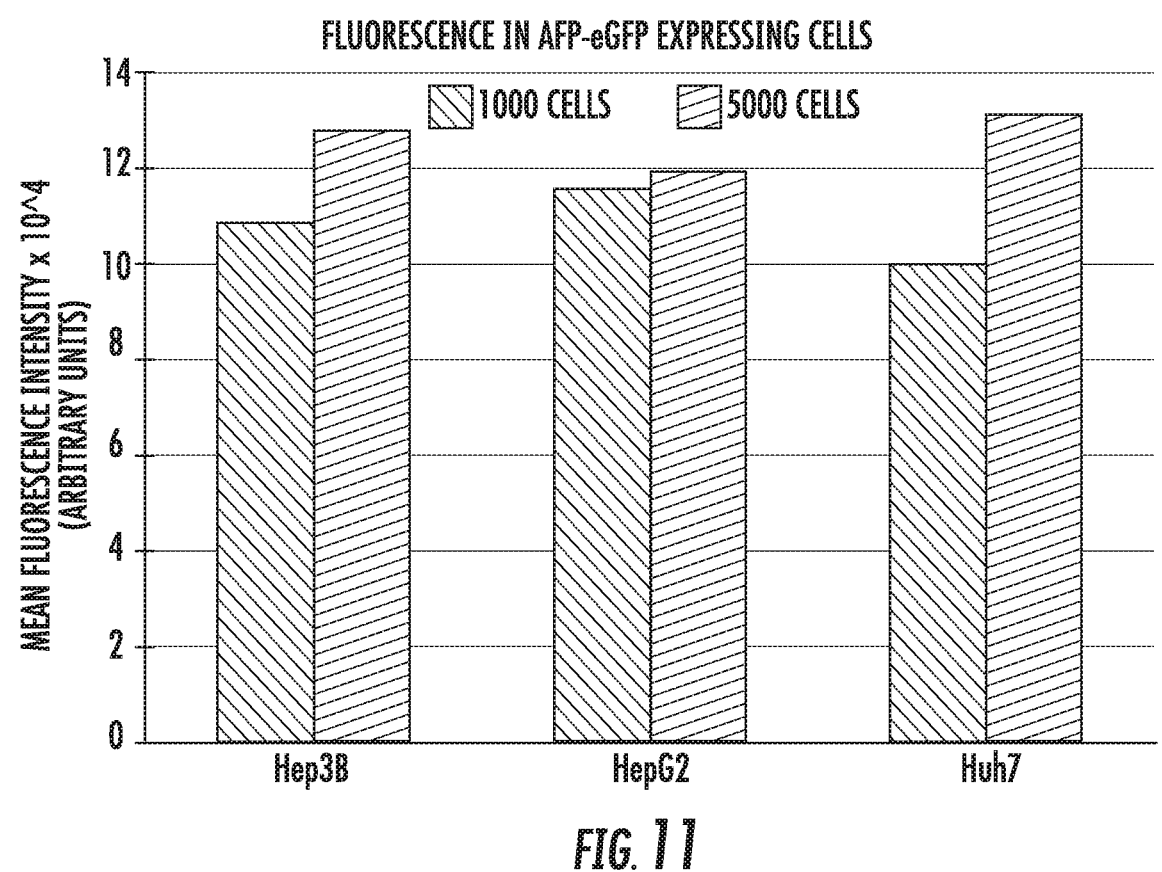
FIG. 11 depicts fluorescence signal intensity in eGFP expressing human HCC cells.

The AFP-promoter driven eGFP plasmid was generated and the transfection was performed using turbofectin reagent (Origene, Truclones Inc). The stable clones positive for eGFP expression were selected using the antibiotic Hygromycin as the selection marker. The positive clones were verified for the expression of eGFP by fluorescence microscopy as well as quantification of green fluorescence in a fluorometer. FIG. 10 shows that human HCC cell lines transfected with eGFP plasmid regulated by human AFP-promoter expressed the green fluorescent protein. Quantitative analysis of fluorescence in a fluorometer (FIG. 11) showed a strong fluorescent intensity in these three cell lines confirming the expression of GFP under AFP-promoter.

FACS Analysis of AFP-Driven Expression of eGFP in Human HCC Cell Lines

Figure 12:
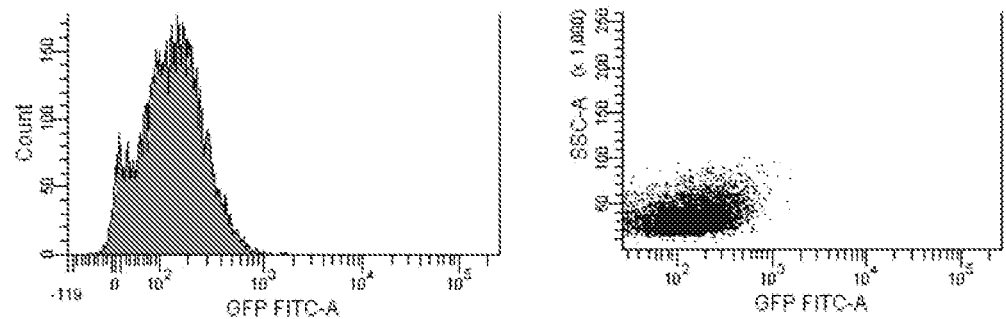
FIG. 12 depicts FACS analysis of Huh7 cell line positive for AFP-dependent eGFP expression.
Figure 13:
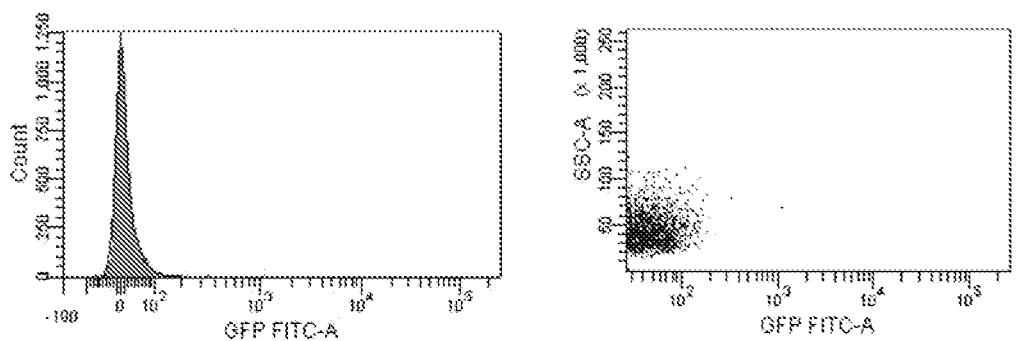
FIG. 13 depicts FACS analysis of HepG2 cell line positive for AFP-dependent eGFP expression.

To further confirm that AFP-promoter driven expression of eGFP in human HCC cell lines can be phenotypically identified, we used Fluorescence-Activated Cell Sorting (FACS) sorting system. Besides microscopic images and quantitative analysis the data from FACS analysis also demonstrated the expression of eGFP in human HCC cell lines. FIG. 12 shows the histogram and scatter plot of number of eGFP-positive Huh7 cells isolated. Similarly, FIG. 13 shows the histogram and scatter graph of eGFP positive HepG2 cells isolated from a population.

The data demonstrate that AFP-promoter driven expression of our gene of interest is feasible and is effective.

Establishment of Luciferase Expressing Human HCC Cells for Bioluminescence Imaging In Vivo In order to monitor tumor cell growth and response to treatment an imagable reporter is very relevant and necessary. Generating cell lines with reporter will enable us to achieve noninvasive imaging of cell growth and viability hence it is critical to generate reporter-based cell lines for downstream applications.

Imagable human HCC cell lines for in vivo application were established by transfecting human HCC cells with imagable-reporter. In brief, the luciferase reporter plasmid was first transfected into human HCC cell lines such as HepG2, Hep3B and Huh7. The resulting transfected cells were selected for stable expression of the luciferase gene by the antibiotic selection marker, Geneticin (G418). The expression of luciferase enzyme was confirmed by bioluminescence imaging in Xenogen Optical Imaging (FIG. 14) and luciferase activity assay in a 96-well plate format (FIG. 15). Cell number dependent increase in BLI intensity both at BLI-image and luciferase activity confirmed the expression of luciferase reporter in these cell lines, and for simplicity here after these cell lines will be referred as luc-HepG2, luc-Hep3B and luc-Huh7.

Figure 14:
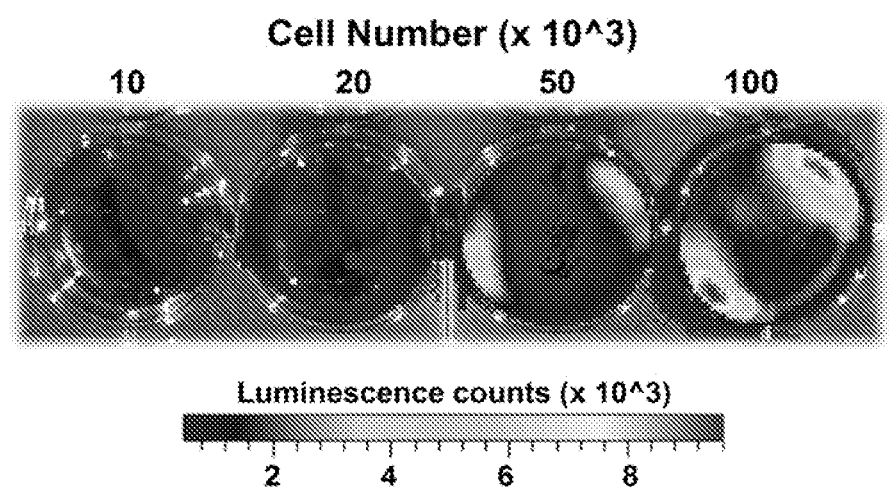
FIG. 14 depicts a representative bioluminescent image of human HCC (Hep3B).
Figure 15:
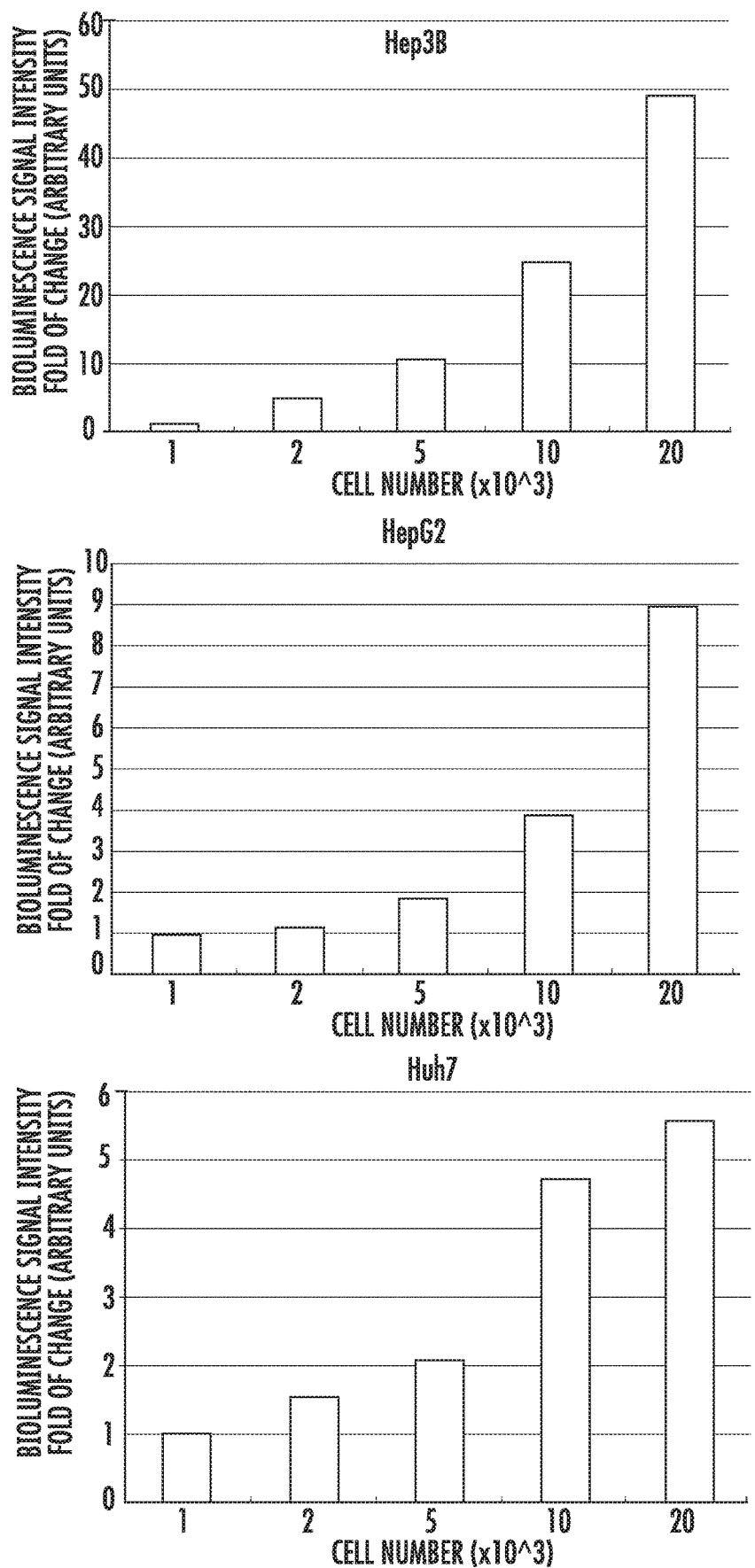
FIG. 15 depicts cell number dependent increase in bioluminescence signal in luc-human HCC cells.

Thus, data from FIGS. 14 & 15, confirmed the luciferase expression in human HCC cell lines which enable us to monitor the tumor growth in vivo. Further, tumor response to therapeutics can also be visualized as a therapy-dependent decrease in luciferase activity (in BLI) will indicate either an arrest of tumor growth and/or apoptosis.

Development of Mutant GAPDH

Figure 16:
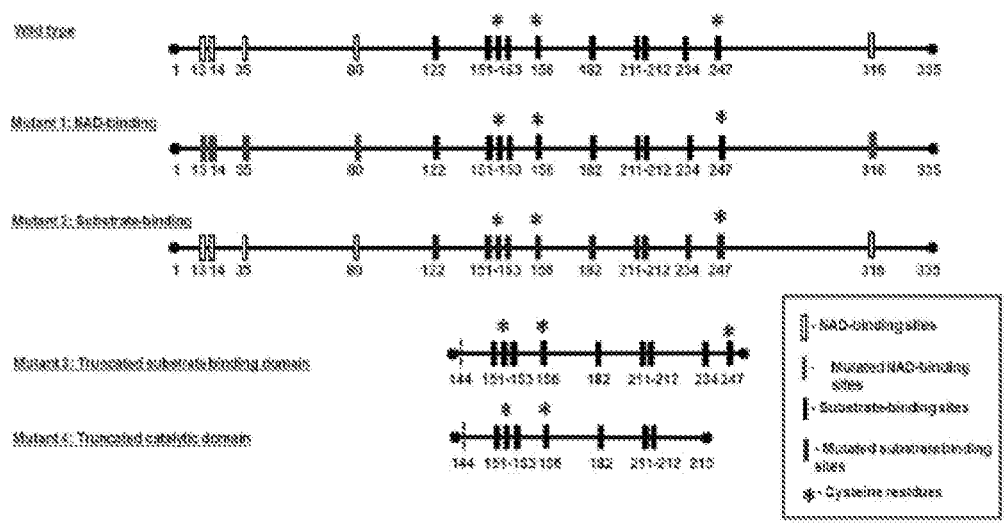
FIG. 16 depicts a schematic showing putative binding sites of NAD and the substrate (GAP) in human GAPDH. The potential for generation of multiple mutants for further screening and selection of an efficient mutant for competitive inhibition.
Figure 19:
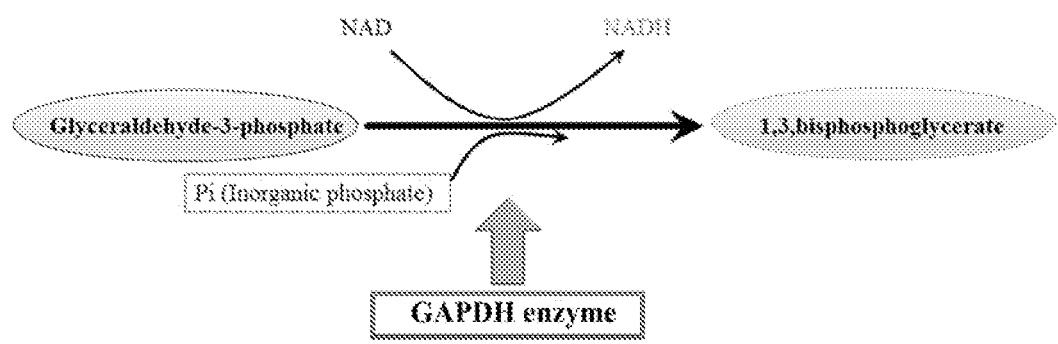
FIG. 19 depicts the enzymatic reaction of GAPDH. GAPDH converts glyceraldehyde-3-phosphate into 1,3-bisphosphoglyceric acid in the presence of NAD and inorganic phosphate. Biochemically, the cysteine residue located in the active, catalytic site modifies the carbonyl group of G-3-P to create a transient hemi-thioacetal molecule. During this process the NAD bound at the specific site close to the catalytic domain accepts hydride ion to get reduced into NADH. Meanwhile the hemi-thioacetal intermediate is concomitantly oxidized in to a thioester which then reacts with inorganic phosphate to form the product 1,3-bisphosphoglyceric acid.
Figure 21:
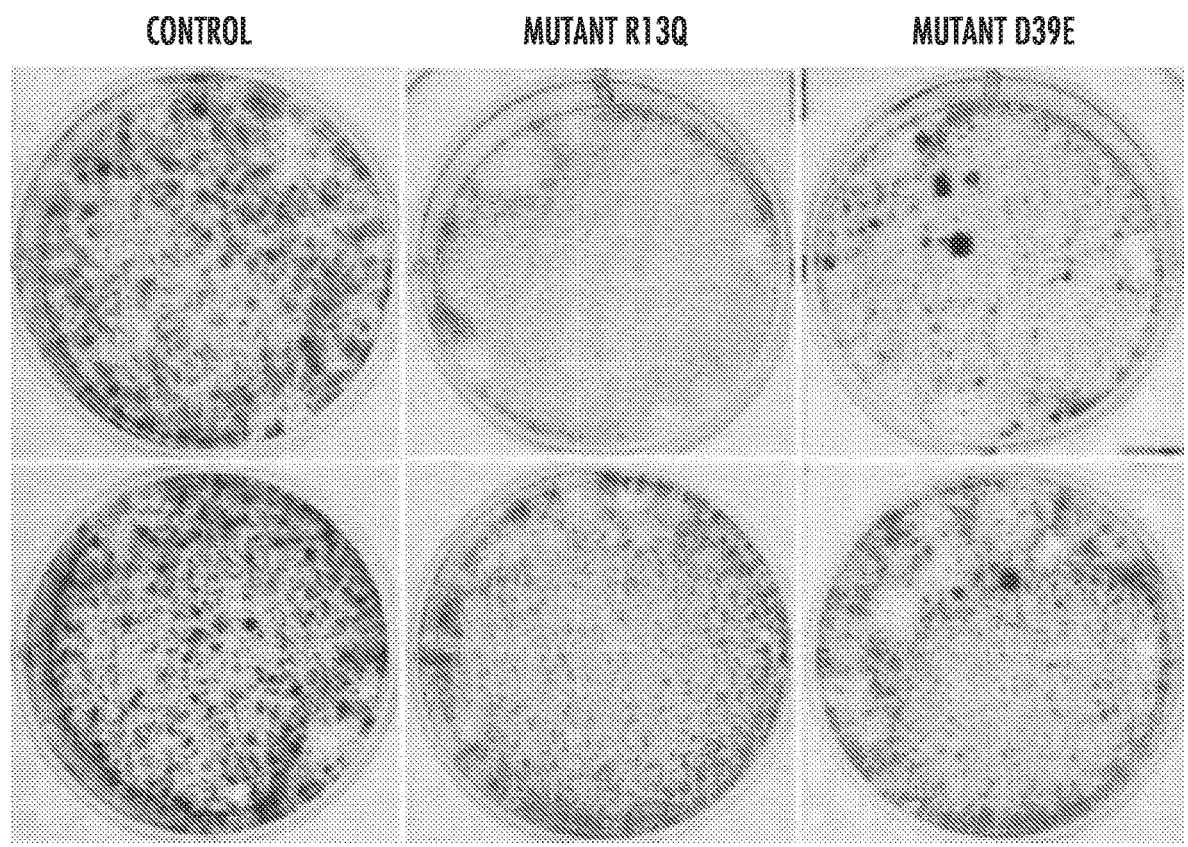
FIG. 21 depicts ectopic expression of mt-R13Q and mt-D39E affects colony formation in human liver cancer cell lines SK-Hep1. Representatives from triplicates are shown.

FIG. 16 shows the schematic of mutant GAPDH that was designed and generated using site directed mutagenesis.

Generation of mt-GAPDH by Site-Directed Mutagenesis

In order to create mutant GAPDH that has mutations at specific amino acid sites we used the Site-directed mutagenesis system. Using a full length wild type human GAPDH plasmid with a myc-DDK tag was procured from Origene Technologies. The myc-DDK tag will enable us to confirm the ectopic expression of GAPDH. The GeneArt Site Directed Mutagenesis kit obtained from Life Technologies Inc., was used with mutations directed at the specific residues as indicated in the schematic (FIG. 16). The mutations were verified by DNA-sequencing and further studies were performed as described below.

Tumor specific inhibition of glycolysis has been documented as a viable therapeutic strategy for treating multiple types of cancers (10-13). GAPDH is one of the glycolytic enzymes that had been known to be involved in several cellular processes in addition to energy metabolism. Further the enzymatic function of GAPDH results in the generation of NADH a critical regulator of intracellular redox balance. Hence the inhibition of GAPDH has profound effect as it affects energy metabolism as well as redox balance. Several inhibitors of glycolysis (e.g. 3-bromopyruvic acid, koningic acid, iodoacetate, methylglyoxal) have been shown to be effective in killing cancer cells in vitro(14). Until our recent report, there was a lacuna in the documentation of GAPDH inhibition in vivo owing to its ubiquitous nature and the related concern of systemic toxicity. We demonstrated that an intratumoral or percutaneous ablation technique could be useful in targeting tumor-GAPDH (4). While the proof-of-principle (i.e.) silencing GAPDH for anticancer effects has been demonstrated, the translational potential of shRNAs has always been met with challenges such as lack of tumor specificity. Here we demonstrate a strategy to circumvent the translational challenges of targeting GAPDH via shRNA or any potent inhibitor, by developing a translatable inhibitory-strategy for selective targeting of tumor-GAPDH using HCC as the tumor model. Precisely, we designed and validated that a nonfunctional mt-GAPDH can compete with tumor-GAPDH for substrate (G-3-P) or coenzyme (NAD) binding resulting in the disruption of glycolytic reaction. To our knowledge this is the first documentation to show that ectopic expression of mutant GAPDH can competitively inhibit glycolysis. Until we saw our data there was little enthusiasm to explore this mutant-GAPDH strategy (i) as competitive inhibition of glycolysis was not expected since cancer cells might compensate for the loss of glycolysis, (ii) rationally, in order to achieve sufficient levels of inhibition of endogenous GAPDH which are in general abundantly expressed a high level of ectopic expression of competing mutant GAPDH will be necessary and finally (iii) as GAPDH is a multifunctional protein it was unclear if blocking its enzymatic function could be sufficient to promote anticancer effects. Thus to our surprise, our data demonstrated that the mutant-GAPDH can promote anticancer phenotypic effects in vivo.

The primary liver cancer, hepatocellular carcinoma (HCC) is one of the most highly lethal malignancies in the world making it the third most common cause of cancer related mortality worldwide (15). Overall survival remains poor (less than 9 months) and largely depends on the stage of the disease. HCC, like other cancer cells, shows increased glucose metabolism, and this tumor specific change in metabolic phenotype is so ubiquitous in cancer, in the clinics it has already been taken advantage to detect or diagnose malignant tumors, using the glucose analog, 2-deoxy glucose (2-DG) by PET imaging.

Recently, it has been demonstrated that in HCC the proliferative activity is tightly correlated with glucose metabolism (16), and both proliferation and metabolism share common regulatory pathways (17), making tumor metabolism an ideal therapeutic target in HCC. One of the enzymes of glucose metabolism, the glyceraldehyde-3-phosphate dehydrogenase (GAPDH), also known as a glycolytic enzyme, has been known to be up-regulated during the progression of HCC (18-19). Multiple lines of evidences also indicate that GAPDH plays pivotal role in several non-glycolytic processes as well (20-21). Corroborating this, several reports have demonstrated that silencing GAPDH by antisense oligonucleotides (5) or small-interfering (si) RNA(6) induces anticancer effects in vitro. Until our recent report there have been no reports of targeting GAPDH in vivo, primarily due to its ubiquitous nature raising the concern of toxicity and non-specific targeting. Using a loco-regional therapeutic approach we demonstrated that GAPDH inhibition by intratumoral injection of naked GAPDH-shRNA affects tumor viability in a mouse model of human HCC (4). However, the translational potential and further progress of such an anti-GAPDH, antiglycolytic approach critically relies on the successful systemic delivery and specific molecular targeting of GAPDH.

As shRNA expression, in general, is regulated by U6 or H1 promoters [of polymerase (III)] and are not tumor-specific, undesirable toxicities remain a major challenge. Further, utilization of tumor-specific promoters for selective expression of shRNA has not yet been successful in clinical translation. In this report document a potential strategy which can circumvent this impasse by a modified, hitherto unknown approach.

Summary

We previously demonstrated using a mouse model of human HCC that intratumoral delivery of GAPDH inhibitors could promote antitumor effects (4). We validated the anti-GAPDH strategy using a small molecule inhibitor (3-bromopyruvate) as well as shRNA (gene silencing) approach. Although few reports have demonstrated that silencing GAPDH promotes cytotoxic effects (5,6) until our report there was no documentation of anti-GAPDH effects in vivo, particularly in human HCC. Although the proof of principle has been established the clinical translation of such anti-GAPDH strategy critically relies on the successful systemic delivery which in turn necessitates tumor specificity and safety (lack of systemic toxicity). In this context, although the 3-bromopyruvate and the GAPDH-shRNA are effective under intratumoral delivery neither of them is specific for cancer hence is likely to cause unwanted toxicity.

With this background, we tested the hypothesis if a mutant GAPDH can interfere with the energy metabolism of cancer resulting in anticancer effects. However, the hypothesis was challenged by major impediments such as (i) a mutant GAPDH may not be effective in blocking the energy metabolism of cancer cells, as GAPDH is an abundant protein and has always known to be over expressed (up-regulated in malignant cells), (ii) GAPDH is a multifunctional protein, hence interfering with its enzyme activity alone may not be sufficient to promote anticancer effects and/or in order to effectively compete with wild type cellular GAPDH an enormous amount of intracellular mutant GAPDH may be necessary, (iii) cancer cells can compensate for the presence of mutant-GAPDH by increasing the expression of wild type GAPDH and finally (iv) tumor specific delivery or expression of mutant GAPDH may not be feasible. Thus these major challenges project the null hypothesis that mutant-GAPDH may not be an effective anticancer agent.

Surprisingly, contrary to our null hypothesis which is based on the major challenges listed above, we found that the mutant GAPDH was sufficient in promoting anticancer effects. Furthermore, of the two types of mutants we tested one of them was more effective than the other the underlying mechanism for which remains unknown. Notably, the delivery of mutant GAPDH intratumorally also showed anticancer effects indicating that mutant-GAPDH indeed is sufficient to block the tumor progression.

We have developed a novel frame-work to develop anticancer strategies and therapeutics to target cancer metabolism and block tumor progression. Here we provide evidence for the first time that ectopic expression of a mutant protein (e.g. GAPDH) is sufficient to compete with cancer cell's GAPDH and block energy metabolism (e.g. Glycolysis). The unique advantage of this strategy is that the expression of mt-GAPDH can be regulated by a tumor specific promoter. For example if we use hTERT promoter for breast cancer, CCKAR promoter for pancreatic cancer and AFP promoter for HCC.

First documentation of a mutant enzyme of glycolytic pathway to interfere with cancer cell's energy metabolism.

Demonstration of a mutant GAPDH to inhibit the enzymatic function of cellular GAPDH The regulation of expression of desired protein of interest (e.g. mutant GAPDH) by tumor specific promoter (e.g. AFP).

The mt-GAPDH may be relevant for any solid malignancy with the use of appropriate tumor-specific promoters. We tested with the promoter of α-feto protein (AFP), a protein marker selectively up regulated in HCC (7) to discover the feasibility.

REFERENCES

1. Hanahan D, Weinberg R A, Hallmarks of cancer: The next generation. Cell. 2011; 144: 646-74.
2. Warburg O. On the origin of cancer cells.—Science. 1956 Feb. 24; 123(3191):309-14.
3. Hugo-Wissemann D, Anundi I, Lauchart W, Viebahn R, de Groot H, Differences in glycolytic capacity and hypoxia tolerance between hepatoma cells and hepatocytes. Hepatology. 1991; 13: 297-303.
4. Ganapathy-Kanniappan S, Kunjithapatham R, Torbenson M S, Rao P P, Carson K A, Buijs M, Vali M, Geschwind J F, Human hepatocellular carcinoma in a mouse model: Assessment of tumor response to percutaneous ablation by using glyceraldehyde-3-phosphate dehydrogenase antagonists. Radiology. 2012; 262: 834-45.
5. Kim J W, Kim T E, Kim Y K, Kim Y W, Kim S J, Lee J M, Kim I K, Namkoong S E, Antisense oligodeoxynucleotide of glyceraldehyde-3-phosphate dehydrogenase gene inhibits cell proliferation and induces apoptosis in human cervical carcinoma cell lines. Antisense Nucleic Acid Drug Dev. 1999; 9: 507-13.
6. Phadke M S, Krynetskaia N F, Mishra A K, Krynetskiy E, Glyceraldehyde 3-phosphate dehydrogenase depletion induces cell cycle arrest and resistance to antimetabolites in human carcinoma cell lines. J Pharmacol Exp Ther. 2009; 331: 77-86.
7. Tyson G L, Duan Z, Kramer J R, Davila J A, Richardson P A, El-Serag H B, Level of alpha-fetoprotein predicts mortality among patients with hepatitis C-related hepatocellular carcinoma. Clin Gastroenterol Hepatol. 2011.
8. Ganapathy-Kanniappan S, Geschwind J F, Kunjithapatham R, Buijs M, Vossen J A, Tchernyshyov I, Cole R N, Syed L H, Rao P P, Ota S, Vali M, Glyceraldehyde-3-phosphate dehydrogenase (GAPDH) is pyruvylated during 3-bromopyruvate mediated cancer cell death. Anticancer Res. 2009; 29: 4909-18.
9. Franken N A, Rodermond H M, Stap J, Haveman J, van Bree C, Clonogenic assay of cells in vitro. Nat Protoc. 2006; 1: 2315-9.
10. Jang M, Kim S S, Lee J, Cancer cell metabolism: Implications for therapeutic targets. Exp Mol Med. 2013; 45: e45.
11. Zhao Y, Butler E B, Tan M, Targeting cellular metabolism to improve cancer therapeutics. Cell Death Dis. 2013; 4: e532.
12. Dang C V. Links between metabolism and cancer. Genes Dev. 2012; 26: 877-90.
13. Ganapathy-Kanniappan S, Geschwind J F, Tumor glycolysis as a target for cancer therapy: Progress and prospects. Mol Cancer. 2013; 12: 152, 4598-12-152.
14. Ganapathy-Kanniappan S, Kunjithapatham R, Geschwind J F, Glyceraldehyde-3-phosphate dehydrogenase: A promising target for molecular therapy in hepatocellular carcinoma. Oncotarget. 2012; 3: 940-53.
15. El-Serag H B. Hepatocellular carcinoma. N Engl J Med. 2011; 365: 1118-27.
16. Kitamura K, Hatano E, Higashi T, Narita M, Seo S, Nakamoto Y, Yamanaka K, Nagata H, Taura K, Yasuchika K, Nitta T, Uemoto S, Proliferative activity in hepatocellular carcinoma is closely correlated with glucose metabolism but not angiogenesis. J Hepatol. 2011; 55: 846-57.
17. Fritz V, Fajas L, Metabolism and proliferation share common regulatory pathways in cancer cells. Oncogene. 2010; 29: 4369-77.
18. Gong Y, Cui L, Minuk G Y, Comparison of glyceraldehyde-3-phosphate dehydrogenase and 28s-ribosomal RNA gene expression in human hepatocellular carcinoma. Hepatology. 1996; 23: 734-7.
19. Lau W Y, Lai P B, Leung M F, Leung B C, Wong N, Chen G, Leung T W, Liew C T, Differential gene expression of hepatocellular carcinoma using cDNA microarray analysis. Oncol Res. 2000; 12: 59-69.
20. Sirover M A. On the functional diversity of glyceraldehyde-3-phosphate dehydrogenase: Biochemical mechanisms and regulatory control. Biochim Biophys Acta. 2011; 1810: 741-51.
21. Tristan C, Shahani N, Sedlak T W, Sawa A, The diverse functions of GAPDH: Views from different subcellular compartments. Cell Signal. 2011; 23: 317-23.
22. Gharwan, H. & Groninger, H. *Nat. Rev. Clin. Oncol.* (2015).
23. Rothenberg, M. L., Carbone, D. P. & Johnson, D. H. *Nat. Rev. Cancer.* 3, 303-309 (2003).
24. Le Tourneau, C., Dieras, V., Tresca, P., Cacheux, W. & Paoletti, X. *Target Oncol.* 5, 65-72 (2010).
25. Pecot, C. V., Calin, G. A., Coleman, R. L., Lopez-Berestein, G. & Sood, A. K. *Nat. Rev. Cancer.* 11, 59-67 (2011).
26. Rayburn, E. R. & Zhang, R. *Drug Discov. Today* 13, 513-521 (2008).
27. Gambhir S S (2002) Molecular imaging of cancer with positron emission tomography. *Nat Rev Cancer* 2: 683-693.
28. Ganapathy-Kanniappan S, Kunjithapatham R, Torbenson M S, Rao P P, Carson K A, Buijs M, Vali M, Geschwind J F (2012) Human hepatocellular carcinoma in a mouse model: assessment of tumor response to percutaneous ablation by using glyceraldehyde-3-phosphate dehydrogenase antagonists. *Radiology* 262: 834-845.
29. Kunjithapatham R, Geschwind J F, Devine L, Boronina T N, O'Meally R N, Cole R N, Torbenson M S, Ganapathy-Kanniappan S (2015) Occurrence of a Multimeric High-Molecular-Weight Glyceraldehyde-3-phosphate Dehydrogenase in Human Serum. *J Proteome Res* 14: 1645-1656.
30. Maher J C, Wangpaichitr M, Savaraj N, Kurtoglu M, Lampidis T J (2007) Hypoxia-inducible factor-1 confers resistance to the glycolytic inhibitor 2-deoxy-D-glucose. *Mol Cancer Ther* 6: 732-741.
31. Mikhaylova M, Mori N, Wildes F B, Walczak P, Gimi B, Bhujwalla Z M (2008) Hypoxia increases breast cancer cell-induced lymphatic endothelial cell migration. *Neoplasia* 10: 380-389.
32. Tan S X, Ng Y, James D E (2010) Akt inhibitors reduce glucose uptake independently of their effects on Akt. *Biochem J* 432: 191-197.

INCORPORATION BY REFERENCE

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

EQUIVALENTS

Although the foregoing subject matter has been described in some detail by way of illustration and example for purposes of clarity of understanding, it will be understood by those skilled in the art that certain changes and modifications can be practiced within the scope of the appended claims.

SEQ ID NO: 3
(DNA) R13Q
ATGGGGAAGGTGAAGGTCGGAGTCAACGGATTTGGTCAAATTGGGCGCCT

GGTCACCAGGGCTGCTTTTAACTCTGGTAAAGTGGATATTGTTGCCATCA

ATGACCCCTTCATTGACCTCAACTACATGGTTTACATGTTCCAATATGAT

TCCACCCATGGCAAATTCCATGGCACCGTCAAGGCTGAGAACGGGAAGCT

TGTCATCAATGGAAATCCCATCACCATCTTCCAGGAGCGAGATCCCTCCA

AAATCAAGTGGGGCGATGCTGGCGCTGAGTACGTCGTGGAGTCCACTGGC

GTCTTCACCACCATGGAGAAGGCTGGGGCTCATTTGCAGGGGGGAGCCAA

AAGGGTCATCATCTCTGCCCCCTCTGCTGATGCCCCATGTTCGTCATGG

GTGTGAACCATGAGAAGTATGACAACAGCCTCAAGATCATCAGCAATGCC

TCCTGGACCACCAACTGGTTAGCACCCCTGGCCAAGGTCATCCATGACAA

CTTTGGTATCGTGGAAGGACTCATGACCACAGTCCTTGCCATCACTGCCA

CCCAGAAGACTGTGGATGGCCCCTCCGGGAAACTGTGGCGTGATGGCCGC

GGGGCTCTCCAGAACATCATCCCTGCCTCTACTGGCGCTGCCAAGGCTGT

GGGCAAGGTCATCCCTGAGCTGAACGGGAAGCTCACTGGCATGGCCTTCC

-continued

```
GTGTCCCCACTGCCAACGTGTCAGTGGTGGACCTGACCTGCCGTCTAGAA
AAACCTGCCAAATATGATGACATCAAGAAGGTGGTGAAGCAGGCGTCGGA
GGGCCCCCTCAAGGGCATCCTGGGCTACACTGAGCACCAGGTGGTCTCCT
CTGACTTCAACAGCGACACCCACTCCTCCACCTTTGACGCTGGGGCTGGC
ATTGCCCTCAACGACCACTTTGTCAAGCTCATTTCCTGGTATGACAAGGA
ATTTGGCTACAGCAACAGGGTGGTGGACCTCATGGCCCACATGGCCTCCA
AGGAGTAA
```

SEQ ID NO: 4
(AA) R13Q

```
M G K V K V G V N G F G Q I G R L V T R A A F N S
G K V D I V A I N D P F I D L N Y M V Y M F Q Y D
S T H G K F H G T V K A E N G K L V I N G N P I T
I F Q E R D P S K I K W G D A G A E Y V V E S T G
V F T T M E K A G A H L Q G G A K R V I I S A P S
A D A P M F V M G V N H E K Y D N S L K I I S N A
S C T T N C L A P L A K V I H D N F G I V E G L M
T T V H A I T A T Q K T V D G P S G K L W R D G R
G A L Q N I I P A S T G A A K A V G K V I P E L N
G K L T G M A F R V P T A N V S V V D L T C R L E
K P A K Y D D I K K V V K Q A S E G P L K G I L G
Y T E H Q V V S S D F N S D T H S S T F D A G A G
I A L N D H F V K L I S W Y D N E F G Y S N R V V
D L M A H M A S K E
```

SEQ ID NO: 5
(DNA) D39E

```
ATGGGGAAGGTGAAGGTCGGAGTCAACGGATTTGGTCAAATTGGGCGCCT
GGTCACCAGGGCTGCTTTTAACTCTGGTAAAGTGGATATTGTTGCCATCA
ATGACCCCTTCATTGAACTCAACTACATGGTTTACATGTTCCAATATGAT
TCCACCCATGGCAAATTCCATGGCACCGTCAAGGCTGAGAACGGGAAGCT
TGTCATCAATGGAAATCCCATCACCATCTTCCAGGAGCGAGATCCCTCCA
AAATCAAGTGGGGCGATGCTGGCGCTGAGTACGTCGTGGAGTCCACTGGC
```

-continued

```
GTCTTCACCACCATGGAGAAGGCTGGGGCTCATTTGCAGGGGGGAGCCAA
AAGGGTCATCATCTCTGCCCCCTCTGCTGATGCCCCCATGTTCGTCATGG
GTGTGAACCATGAGAAGTATGACAACAGCCTCAAGATCATCAGCAATGCC
TCCTGGACCACCAACTGGTTAGCACCCCTGGCCAAGGTCATCCATGACAA
CTTTGGTATCGTGGAAGGACTCATGACCACAGTCCTTGCCATCACTGCCA
CCCAGAAGACTGTGGATGGCCCCTCCGGGAAACTGTGGCGTGATGGCCGC
GGGGCTCTCCAGAACATCATCCCTGCCTCTACTGGCGCTGCCAAGGCTGT
GGGCAAGGTCATCCCTGAGCTGAACGGGAAGCTCACTGGCATGGCCTTCC
GTGTCCCCACTGCCAACGTGTCAGTGGTGGACCTGACCTGCCGTCTAGAA
AAACCTGCCAAATATGATGACATCAAGAAGGTGGTGAAGCAGGCGTCGGA
GGGCCCCCTCAAGGGCATCCTGGGCTACACTGAGCACCAGGTGGTCTCCT
CTGACTTCAACAGCGACACCCACTCCTCCACCTTTGACGCTGGGGCTGGC
ATTGCCCTCAACGACCACTTTGTCAAGCTCATTTCCTGGTATGACAAGGA
ATTTGGCTACAGCAACAGGGTGGTGGACCTCATGGCCCACATGGCCTCCA
AGGAGTAA
```

SEQ ID NO: 6
(AA) D39E

```
M G K V K V G V N G F G R I G R L V T R A A F N S
G K V D I V A I N D P F I E L N Y M V Y M F Q Y D
S T H G K F H G T V K A E N G K L V I N G N P I T
I F Q E R D P S K I K W G D A G A E Y V V E S T G
V F T T M E K A G A H L Q G G A K R V I I S A P S
A D A P M F V M G V N H E K Y D N S L K I I S N A
S C T T N C L A P L A K V I H D N F G I V E G L M
T T V H A I T A T Q K T V D G P S G K L W R D G R
G A L Q N I I P A S T G A A K A V G K V I P E L N
G K L T G M A F R V P T A N V S V V D L T C R L E
K P A K Y D D I K K V V K Q A S E G P L K G I L G
Y T E H Q V V S S D F N S D T H S S T F D A G A G
I A L N D H F V K L I S W Y D N E F G Y S N R V V
D L M A H M A S K E
```

---

What is claimed:

1. An isolated polypeptide molecule comprising a mutant full-length, human glyceraldehyde-3-phosphate dehydrogenase (GAPDH), wherein the mutation comprises at least one of (a) an arginine to glutamine change at amino acid position 13; and (b) an aspartic acid to glutamic acid change at amino acid position 39.

2. The isolated polypeptide molecule of claim 1, wherein the mutant full-length, human GAPDH comprises an arginine to glutamine change at amino acid position 13 comprises SEQ ID NO:4.

3. The isolated polypeptide molecule of claim 1, wherein the mutant full-length, human GAPDH comprises an aspartic acid to glutamic acid change at amino acid position 39 comprises SEQ ID NO:6.

4. A pharmaceutical composition comprising the isolated polypeptide molecule of claim 1, in combination with a pharmaceutically acceptable carrier or adjuvant.

* * * * *